US011389086B2

(12) United States Patent
Mulheran et al.

(10) Patent No.: US 11,389,086 B2
(45) Date of Patent: Jul. 19, 2022

(54) APPARATUS AND METHODS FOR ASSESSING THE EFFECT OF LIGHT ON A SUBJECT'S PERCEPTION OF TINNITUS

(71) Applicants: University of Leicester, Leicester (GB); Orthoscopics Limited, Cambridge (GB); Nicolette Sophia Dorothea Street, Pontypridd (GB)

(72) Inventors: Michael Mulheran, Leicester (GB); John Anderson, Cambridge (GB); Graham Street, Cambridge (GB); Ian Jordan, Cambridge (GB)

(73) Assignees: University of Leicester, Leicester (GB); Orthoscopics Limited, Cambridge (GB)

( * ) Notice: Subject to any disclaimer, the term of this patent is extended or adjusted under 35 U.S.C. 154(b) by 382 days.

(21) Appl. No.: 16/727,342

(22) Filed: Dec. 26, 2019

(65) Prior Publication Data

US 2020/0205700 A1  Jul. 2, 2020

Related U.S. Application Data

(63) Continuation of application No. 14/112,715, filed as application No. PCT/EP2012/057704 on Apr. 26, 2012, now abandoned.

(30) Foreign Application Priority Data

Apr. 26, 2011 (GB) .............................. GB1106882.2

(51) Int. Cl.
*A61B 5/12* (2006.01)
*A61B 5/00* (2006.01)
*A61B 5/16* (2006.01)

(52) U.S. Cl.
CPC ............. *A61B 5/128* (2013.01); *A61B 5/0059* (2013.01); *A61B 5/4848* (2013.01); *A61B 5/165* (2013.01); *F04C 2270/041* (2013.01)

(58) Field of Classification Search
CPC ..... A61B 5/128; A61B 5/0059; A61B 5/4848; A61B 5/165; A61B 3/02; A61B 3/066; A61N 2005/0663; A61N 2005/0648
See application file for complete search history.

(56) References Cited

U.S. PATENT DOCUMENTS

| 6,802,608 B1 | 10/2004 | Tamai et al. |
| 2003/0004499 A1 | 1/2003 | McDaniel |

(Continued)

FOREIGN PATENT DOCUMENTS

| WO | WO-88/10088 A1 | 12/1988 |
| WO | WO-2009/050213 A1 | 4/2009 |
| WO | WO-2009/074624 A1 | 6/2009 |

OTHER PUBLICATIONS

Landgrebe, et al., "Effects of colour exposure on auditory and somatosensory perception-hints for cross-modal plasticity", Neuro endocrinology letters, vol. 29, No. 4, Aug. 2008, pp. 518-521.

(Continued)

*Primary Examiner* — Devin B Henson
(74) *Attorney, Agent, or Firm* — Henry Patent Law Firm PLLC

(57) ABSTRACT

A method of assessing the effect of viewing varying colours of light on a subject's perception of tinnitus, comprising the steps of: presenting a display in at least part of the subject's field of view; illuminating the display with coloured light in the visible spectrum using one or more variable sources, varying measurable values of the coloured light illuminating the display; and recording the measurable values of the coloured light illuminating the display at which the subject indicates a change in their perception of tinnitus. Also (Continued)

provided are methods of determining which tristimulus values of light can be used to alleviate a subject's perception of tinnitus, methods of producing data sets of measurable values of coloured light, use of coloured light, articles formulated to modify illumination of at least part of the visual field of a subject, a method of alleviating a subject's perception of tinnitus and use of apparatus for assessing the effect of viewing varying colours of light on a subject's perception of tinnitus.

15 Claims, 36 Drawing Sheets

(56) References Cited

U.S. PATENT DOCUMENTS

| | | |
|---|---|---|
| 2003/0011832 A1 | 1/2003 | Chang |
| 2003/0223036 A1 | 12/2003 | Anderson et al. |
| 2006/0098077 A1 | 5/2006 | Dowling |
| 2007/0167999 A1 | 7/2007 | Breden et al. |
| 2007/0273827 A1 | 11/2007 | Matsuo et al. |
| 2009/0099476 A1 | 4/2009 | Fogel et al. |
| 2011/0063572 A1 | 3/2011 | Legatt |
| 2011/0227818 A1 | 9/2011 | Su |

OTHER PUBLICATIONS

Görlach, Tobias, "International Search Report" for PCT/EP2012/057704, dated Aug. 24, 2012, 5 pages.

APPARATUS AND METHODS FOR ASSESSING THE EFFECT OF LIGHT ON A SUBJECT'S PERCEPTION OF TINNITUS

This application is a Continuation of U.S. patent application Ser. No. 14/112,715, filed on Apr. 26, 2012. U.S. application Ser. No. 14/112,715 is a national-stage application of PCT Application No. PCT/EP2012/057704. PCT Application No. PCT/EP2012/057704 claims priority from United Kingdom Application No. GB1106882.2, filed on Apr. 26, 2011. The entire contents of these applications are incorporated herein by reference in their entirety.

The present invention relates to methods for assessing the effect of viewing varying colours of light on a subject's perception of tinnitus. It further relates to use of coloured light in the treatment of tinnitus, articles formulated to modify illumination of at least part of the visual field of a subject and methods of alleviating a subject's perception of tinnitus.

Tinnitus is a condition which affects a wide range of people and relates to a person's perception of sound within the ear which does not result from any corresponding external source. This sound is commonly perceived as a ringing, whistling, humming or buzzing noise in the head and/or one or both of the ears. Tinnitus frequently arises following acute or chronic ototrauma, such as occupational noise exposure, bacteria meningitis and ototoxic drugs, as a side effect of the use of such medication, or can be an indication of something more sinister such as acoustic neuromas or glomous tumours.

It is a highly prevalent condition affecting a large number of people throughout the world. Furthermore, conservative estimates suggest that about 1% of the population in Europe and the US suffer from chronic tinnitus serious enough to affect quality of life.

Tinnitus may be either intermittent or continuous and, in the worst cases, can lead to fatigue, sleep deprivation, irritability and/or clinical depression, causing significant distress and discomfort to its sufferers. Furthermore, sufferers can find that their tinnitus can limit their ability to hear external sounds which occur within the same range as the frequency of the sound perceived as tinnitus, thereby leading to an additional hearing deficit.

There are two ways in which tinnitus may be treated: a) by treating the underlying cause, for example if tinnitus is found to be a consequence of a specific condition; or b) by providing symptomatic relief regardless of the underlying cause. Treatments which fall into the latter group are used either when the underlying cause is unknown and/or it cannot be treated. The present invention is concerned with such treatments that provide symptomatic relief to tinnitus.

In some sufferers, it has been found that the intensity of tinnitus may be changed by movement of the head, shoulders, jaws, tongue or eye. Accordingly, this offers a way in which a person can self-treat themselves to alleviate the intensity of the sound. However, as will be appreciated in some situations, it will not be suitable for a person to change their movements to lessen the intensity of tinnitus and so such treatment is not always possible.

At present, there is no treatment available which is specifically designed to target tinnitus. The treatments currently being prescribed to provide symptomatic relief include hearing aids, off-label pharmaceuticals and/or counseling therapy, known as tinnitus retraining therapy (TRT). However, each of these therapies have drawbacks and have relatively low success rates as only a small fraction of tinnitus sufferers experience the benefits thereof.

The use of hearing aids, for instance, is only suitable for people who experience hearing loss within the frequency range of their tinnitus. A hearing aid improves/optimises hearing and so takes the sufferer's attention away from the sound produced by tinnitus. In particular, it amplifies sounds in the middle and inner ear to increase the loudness of ambient sounds to mask the discomfort caused by tinnitus.

Additionally, there may be some social stigma associated with wearing such tinnitus maskers which will deter a significant number of sufferers from wearing them, particularly if they are relatively young. Furthermore, in addition to the fact that hearing aids are only suitable for sufferers who experience hearing loss, it has been found that there are a number of sufferers for which the hearing aids do not have the anticipated effect. As will be appreciated, such course of treatment can be relatively costly due to the cost of the hearing aids themselves, the need to frequently replace the miniature batteries and the cost of the clinician for subsequent aftercare.

An alternative treatment may involve the prescribed use of off-label pharmaceuticals. By "off-label pharmaceuticals" it is meant drugs that are primarily intended to treat another condition but which have been found to be effective in providing symptomatic relief for tinnitus. Examples of drugs that may be prescribed off-label include anti-anxiety drugs, antidepressants, antihistamines, anticonvulsants and even some anaesthetics.

The disadvantages associated with the use of off-label pharmaceuticals in the treatment of tinnitus includes the probability of some patients suffering adverse side effects to the drugs, the relatively low success rates, mainly due to the fact that these drugs are not designed specifically for the treatment of tinnitus, and the necessity to continue taking the drugs, even if the patient is not suffering the effects of tinnitus at the time.

A further method currently used to treat tinnitus is tinnitus retraining therapy (TRT). TRT is a type of counseling therapy which aims to change a patient's perception of tinnitus by a combination of explanation, counseling and the controlled use of white noise generators or hearing aids. Although such treatment does not put the patient at risk of adverse side effects, compared with drugs, tinnitus specialists are generally sceptical of the efficacy and cost effectiveness of such treatments.

Accordingly, there exists a need to provide a new and improved treatment for providing symptomatic relief to sufferers of tinnitus, which does not suffer the disadvantages of existing treatments as described above. In particular, it would be advantageous to provide a method of treatment which is effective for a greater proportion of tinnitus sufferers, can be administered by the patient to reduce costs and/or has minimal or no adverse side effects.

According to a first aspect of the present invention there is provided a method of assessing the effect of viewing varying colours of light on a subject's perception of tinnitus, comprising the steps of:
  presenting a display in at least part of the subject's field of view;
  illuminating the display with coloured light in the visible spectrum using one or more variable sources;
  varying measurable values of the coloured light illuminating the display; and
  recording the measurable values of the coloured light illuminating the display at which the subject indicates a change in their perception of tinnitus.

The inventors have surprisingly found that coloured light can be used to treat all categories of tinnitus sufferers, in particular chronically diagnosed sufferers of tinnitus, providing an initial success rate of 40%, without reporting any adverse side effects. The present invention provides a method for determining measurable values of coloured light which positively affects a subject's perception of tinnitus. By varying the measurable values of the coloured light observed by the subject using one or more variable sources, the coloured light can be finely tuned to a point at which a change in their perception of tinnitus is detected. If a certain coloured light is found to adversely effect a subject's perception of tinnitus, this can be omitted from further investigation with no lasting effect to the subject. The measurable values determined by the method of the present invention can then subsequently be used in the treatment of the condition.

In one embodiment, the measurable values are tristimulus values of the coloured light entering the subject's eye. The tristimulus values of coloured light are dependent upon documented peak cone cell sensitivities and define the amounts of the three primary colours (i.e. red, blue and green) present as an additive mixture in the coloured light entering the subject's eye. These values correspond to a single point on a CIE1931 Standard Observer colour space and can be determined by standard techniques where the wavelengths of Red, Green and Blue light are determined by the method of the present invention and the spectral power distribution of the illumination is known from the settings of the apparatus used.

Alternatively, the measurable values may be mixtures of wavelengths making up the coloured light, i.e. the wavelengths of Red, Green and Blue light present in the coloured light.

The one or more variable sources preferably comprise one or more narrowband coloured light sources. As will be appreciated, a narrowband coloured light source is a source having narrow band gaps across which electrons pass, causing the light source to emit coloured light. As a result of the narrow band gaps, the light source has a high spectral resolution, thus ensuring a high level of specificity in the measurement of the wavelengths or tristimulus values of the light produced. In contrast, broadband light sources have much greater band gaps and so the measurable values of the coloured light produced by such sources cannot be measured to the same degree of specificity, and so have relatively low spectral resolutions.

The one or more variable sources may be in the form of a colour controllable light source or a computer program which is designed to present coloured light of varying measurable values on a computer screen (i.e. display). In a preferred embodiment, said one or more variable sources may be a colour controllable light source having at least one narrowband coloured light source. As will be appreciated, said at least one narrowband coloured light source may be a broadband spectrophotometric visible light adapted to produce narrowband coloured light, for example, a mercury light incorporating a narrowband slit filter. However, for energy efficiency and safety considerations, said at least one narrowband coloured light source is preferably at least one narrowband semiconductor light source, such as a light-emitting diode (LED). In a particularly preferred embodiment, the colour controllable light source comprises at least two narrowband coloured light sources, more preferably at least three narrowband coloured light sources, which each emit different spectral components within the visible light spectrum.

The colour controllable light source may be configured to be connected to a control unit and/or a computer and designed to present coloured light on an independent display. Alternatively, the colour controllable light source may be incorporated into a computer, laptop or the like and designed to present coloured light on the visual display unit of the computer, laptop or the like.

In a preferred embodiment, the steps of the method are repeated at least once to ensure reliability of the results.

Preferably, the method further comprises the step of prescribing use of an article formulated to modify illumination of at least part of the visual field of the subject such that coloured light having the measurable values determined by the method is observed.

According to a second aspect of the present invention, there is provided a method of determining which tristimulus values of light can be used to alleviate a subject's perception of tinnitus comprising the steps of:

presenting a display in at least part of the subject's field of view;

illuminating the display with light in the visible spectrum using one or more variable sources;

varying the tristimulus values of the light illuminating the display; and recording the tristimulus values of the light illuminating the display where the subject indicates a change in their perception of tinnitus.

According to a third aspect of the present invention, there is provided a method of determining which tristimulus values of coloured light can be used to alleviate a subject's perception of tinnitus comprising the steps of:

presenting a display in at least part of the subject's field of view;

illuminating the display with coloured light in the visible spectrum using one or more variable sources;

varying the output of said one or more variable sources to provide a mixture of wavelengths making up the coloured light illuminating the display;

recording the mixture of wavelengths of the coloured light illuminating the display where the subject indicates a change in their perception of tinnitus; and determining the tristimulus value of the coloured light at which a change was detected from the mixture of wavelengths.

The output of said one or more variable sources which can be varied may be the intensities and/or wavelengths thereof.

The use of one or more variable sources, as described above, allows the coloured light entering the subject's eye to be tailored to a subject's cone sensitivities at which the brain perceives an improvement in the subject's perception of tinnitus. By determining the wavelengths of each component of light, i.e. the three primary colours (Red, Blue and Green) present in the coloured light, these provide the ratio of the separate components of the coloured light and so enable determination of the tristimulus values associated with the cone sensitivities.

According to a fourth aspect of the present invention, there is provided a method of producing a data set of measurable values of coloured light comprising the steps of:

presenting coloured light in a subject's field of view;

varying the colour of the light in the subject's field of view; and recording said measurable values of the coloured light at at least one point at which the subject perceives a non-visual change.

As observed in the examples provided below, a subject may perceive an improvement in their perception of tinnitus at more than one point in colour space and so there may be more than one set of measurable values (such as tristimulus values or mixtures of wavelengths) associated with these improvements which can be used in the treatment of tinnitus.

According to a fifth aspect of the present invention, there is provided a method of producing a data set of defined measurable values of coloured light comprising the steps:
presenting to a subject coloured light with defined measurable values;
altering said defined measurable values; and
recording said defined measurable values when the subject indicates a change in their non-visual perception.

According to a sixth aspect of the present invention, there is provided use of coloured light having a predetermined mixture of wavelengths in the treatment of tinnitus.

According to a seventh aspect of the present invention, there is provided use of coloured light with one or more predetermined tristimulus values in the treatment of tinnitus.

According to an eighth aspect of the present invention, there is provided use of a composition of photons of one or more predetermined wavelengths in the treatment of tinnitus.

In the present invention, the term "a composition of photons" is used to define a plurality of photons of one or more predetermined wavelengths used as a composition to produce coloured light for use in the treatment of tinnitus.

According to a ninth aspect of the present invention, there is provided an article formulated to modify illumination of at least part of the visual field of a subject such that coloured light having a data set of measurable values determined by either of the methods described above is observed for alleviation of a subject's perception of tinnitus.

In one embodiment, the article may be a filter designed to allow only coloured light having said measurable values, for example the tristimulus values, determined by the methods described above to pass therethrough. Such a filter may be a coating suitable for application to spectacles, a white light source or a suitably calibrated light source. As will be appreciated, a standard light source does not emit pure white light and may typically have the blue region of the colour spectrum removed altogether. Accordingly, by "a suitably calibrated light source", it is meant that the output of the light source has been determined and the coating has been adapted to compensate for any variations from pure white light of the output, thus ensuring that coloured light of the predetermined measurable values is observed in use.

In an alternative embodiment, the article may comprises at least one narrowband coloured light sources configured to produce coloured light having said measurable values (i.e. the mixture of wavelengths or tristimulus values) determined by any of the methods described above. In this way, a single LED device could be tuned to provide the necessary mixture of wavelengths and/or tristimulus values. However, the article preferably comprises at least two, more preferably three, narrowband coloured light sources, the outputs of which are mixed to produce the coloured light having the predetermined measurable values.

The article of the above embodiment is preferably in the form of a light source comprising the at least one narrowband coloured light source. Such a light source is capable of producing low level coloured light of a predetermined mixture of wavelengths and/or tristimulus values. Preferably, the light source comprises at least one red LED, at least one blue LED and at least one green LED. Accordingly, mixing the output of the red, blue and green LEDs produces coloured light having a specific mixture of wavelengths/tristimulus values and avoids colour blotches and fringing.

In one or more embodiments, said light source may further comprise a means for mixing the output of the red, blue and green LEDs, more preferably said means is a diffuser.

The light source may be incorporated into a laptop-like folding device having a backlit screen; a headset designed to be placed over the user's eyes; a handset, for example a small screen or a garment designed to cover at least part of the user's hand, designed to be held up to or against the user's eyes; a projector having a detachable diffuser and white reflector so that the user can look directly at the projector when the diffuser is attached, or so that the user can look at the white reflector when the diffuser is detached; or a nightlight comprising a diffuser, which the user can look at directly. By "nightlight" it is meant a light for use in a dark space, i.e. a space without the presence of any other ambient lighting. Preferably, the light source comprises a memory capable of storing at least one data set for a mixture of wavelengths/tristimulus values of coloured light, i.e. an internal memory. In this way the light source can be pre-programmed with the measurable values of light at which the tinnitus sufferer perceived an improvement in their perception of tinnitus for immediate use. This pre-programming may be undertaken either during manufacture or at any point in the lifetime of the light source, for example by connecting the light source to a computer and installing the relevant data set via a USB cable.

More preferably, the memory is capable of storing a plurality of data sets or measurable values for coloured light. This is particularly preferred where the subject has perceived an improvement in their perception of tinnitus at more than one point in colour space. In one embodiment the light source can automatically switch between the pluralities of predetermined data sets of coloured light. However, preferably the user can switch between the pluralities of predetermined data sets manually, for example by use of a series of push buttons, each button associated with a data set, or by use of an interactive menu on a user interface.

Where the light source is in the form of a nightlight, the nightlight may further comprise a projection means for projecting the coloured light produced by the at least one narrowband coloured light source onto an external surface within the subject's visual field. Such a nightlight will therefore provide general lighting coverage of a space as opposed to a standard dome-shaped lamp, whose brightness may be unpleasant and which would lose effectiveness as the subject moves away from such a lamp, causing the tinnitus to return. The projection means may be angled to project coloured light into the subject's visual field. Preferably the nightlight further comprises a baffle for positioning about the projection means to minimise direct lighting effects and glare.

Preferably the nightlight is configured to compensate for a non-white external surface onto which the coloured light is to be projected to ensure that the coloured light observed by the subject is at the pre-determined data set values. The nightlight may be configured in such a way to adapt the red, green and blue settings to compensate for the colour of the surface. Accordingly, in the event of a non-white external display surface, the user is able to configure the nightlight by making the necessary adjustments to the red, green and blue settings to compensate for a tint variation. In this way, the subject will perceive an improvement in their perception of tinnitus regardless of the surrounding environment.

In view of the level of precision required in producing coloured light having specifically predetermined values, the light source is preferably capable of self-calibration. This is necessary due to the significant wavelength and brightness variability of the at least one narrowband coloured light source, which would lead to variations in the pre-determined coloured light produced by the light source over time. Self-calibration may be achieved by installing the required information to convert the light source to a notional repeatable "perfect" light source into software within the device or a computer to which the light source is configured to be connected to at manufacture.

Furthermore, the p-n junction of the at least one narrowband coloured light source may be prone to self-heating during use, which effects proportional shifts in the wavelengths of coloured light produced by the narrowband coloured light source. Accordingly, in order to prevent such shifts in the wavelengths and ensure that coloured light observed by the subject is at the pre-determined data set values, the light source may comprise regulator electronics which effect thermal dissipation of the p-n junctions, thereby controlling the relationship between the p-n junction temperature and the wavelength of the desired light output. Particularly preferred regulator electronics include a voltage regulator or a switched mode power supply. It is preferable that an independent spectrometer reading is taken at regular intervals to ensure that the regulator electronics are performing adequate thermal dissipation to maintain a constant, predefined output.

According to a tenth aspect of the present invention, there is provided a method of alleviating a subject's perception of tinnitus comprising:
    providing an article formulated to modify illumination of at least part of the visual field of the subject, to provide coloured light having measurable values determined by the method of claim 1; and
    exposing the subject to the coloured light having the predetermined measurable values, to alleviate the subject's perception of tinnitus.

As opposed to treatment with drugs, the treatment of the present invention can be used on an ad hoc basis, when a subject's tinnitus is intensified and unbearable, therefore, preventing any unnecessary use. This therefore makes such a treatment preferable over the use of any drugs and commercially viable.

A further advantage of the method of treatment of the present invention is that the costs associated with such a treatment are relatively low when compared to those of use hearing aids and TRT, as once formulated to the predetermined measurable values, the article can be used by the tinnitus sufferer with little clinical intervention.

According to an eleventh aspect of the present invention, there is provided use of apparatus for assessing the effect of viewing varying colours of light on a subject's perception of tinnitus, the apparatus comprising:
    a display disposed in at least part of the subject's field of view;
    one or more variable sources configured to illuminate the display with coloured light in the visible spectrum;
    a means for varying measurable values of the one or more variable sources to produce coloured light in the visible spectrum; and
    a device for determining said measurable values of the coloured light produced by the one or more variable sources.

Preferably, the one or more variable sources comprise one or more narrowband coloured light sources. The one or more variable sources may be a colour controllable light source having at least two narrowband coloured light sources, each of which is configured to emit a respective spectral component of the visible spectrum.

In a preferred embodiment of the eleventh aspect of the present invention, there is provided use of apparatus for assessing the effect of viewing varying colours of light on a subject's perception of tinnitus, the apparatus comprising:
    a display disposed in at least part of the subject's field of view;
    a colour controllable light source having at least two narrowband coloured light sources, each of which is configured to emit a respective spectral component of the visible spectrum;
    a means for varying measurable values of the at least two narrowband coloured light sources to produce an additive combination of the spectral components; and
    a device for determining said measurable values of said additive combination produced by the colour controllable light source.

The colour controllable light source may preferably have at least three narrowband coloured light sources such that the apparatus is capable of searching throughout the entire colour space to find the measurable values which are associated with a change, preferably an improvement, in the subject's perception of tinnitus.

As indicated above, the colour controllable light source may be a device configured to be connected to a control unit and/or a computer and designed to present coloured light on an independent display. Alternatively, the colour controllable light source may be incorporated into a computer, laptop or the like and the display may be the visual display unit of the computer, laptop or the like, so that the colour controllable light source is designed to present coloured light on the visual display unit.

As will be appreciated, the features of the apparatus employed in the method of the first aspect of the present invention may apply equally to the subsequent aspects of the present invention, without limitation.

Embodiments of the present invention will now be described, by way of example only, with reference to the accompanying figures in which.

Figure 1:
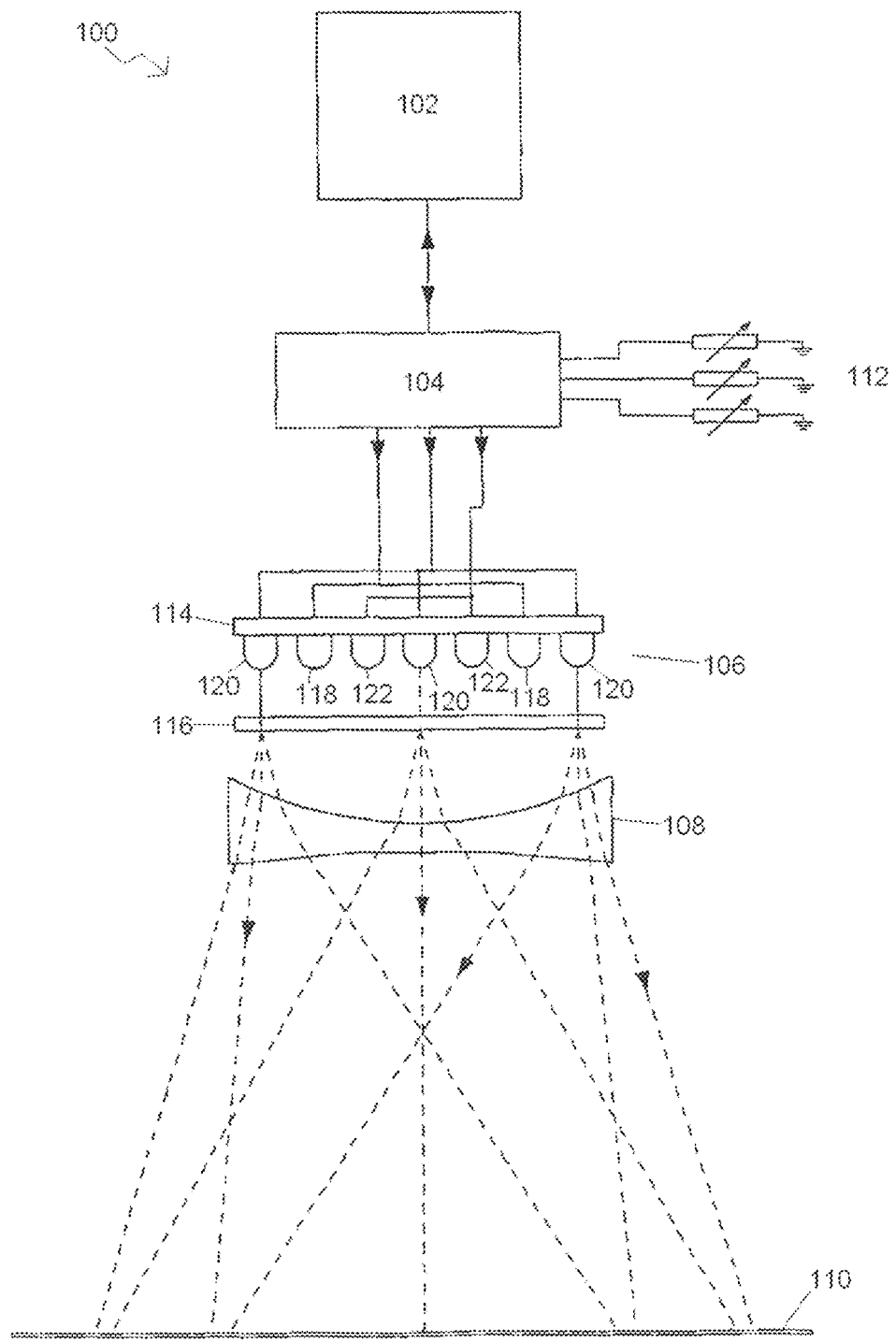
FIG. 1 is a schematic representation of apparatus suitable for use in one embodiment of the method of the present invention.

With reference to FIG. 1 there is shown apparatus 100 for assessing a subject's perception of tinnitus in accordance with an embodiment of the method of the present invention.

Apparatus 100 comprises a computer 102, a control unit 104 having three variable resistors 112, one or more variable sources in the form of a colour controllable light source 106 having a plurality of narrowband coloured light sources 114, a diffuser 116 and divergence lens 108. Apparatus 100 is configured to illuminate a display 110.

Computer 102 provides a means by which the apparatus 100 can monitor the measurable values of coloured light produced by colour controllable light source 106. This allows the computer to record the relevant measurable values of the coloured light at which an improvement in the subject's perception of tinnitus is observed. In this embodiment, the computer 102 is monitoring and recording the mixture of wavelengths of the light emitted from the narrowband coloured light sources 114 of the colour controllable light 106. Furthermore, the computer 102 provides a means of storing information regarding the coloured light identified to have the most improved effect on the subject's perception of tinnitus.

Control unit 104 is typically a microprocessor which receives a number of different inputs from variable resistors 112 to control the output of the colour controllable light source 106. Variable resistors 112 are provided with a corresponding non-graticulated dial (not shown) located at an external surface of the apparatus 100 by which the subject can selectively control the output of the colour controllable light source 106 via control unit 104. Control unit 104 is connected to computer 102 to relay the values of the number of different inputs controlling the output of the colour controllable light source 106 for analysis and storage.

As stated above, colour controllable light source 106 comprising a plurality of narrowband coloured light sources 114 and a diffuser 116. The plurality of narrowband coloured light sources 114 is an array of LEDs comprising red emitters 118, having an emission spectrum peaking at 640 nm, green emitters 120, having an emission spectrum peaking at 524 nm, and blue emitters 122, having an emission spectrum peaking at 470 nm. The distribution of red, green and blue emitters depend upon the power of each type and so should be balanced, i.e. more emitters which have relatively low power and less emitters which are more high power, to achieve a uniform range of white light in the middle of the available colour and intensity fields.

One of the three variable resistors 112 correspond to each of the different emitters. For example, the first variable resistor corresponds to the red emitters, the second variable resistor corresponds to the green emitters and the third variable resistor corresponds to the blue emitters. In this way, the subject can adjust the tint of the output of the array of LEDs to tune the colour controllable light source to the measurable values at which there is an improvement in the subject's perception of tinnitus.

Diffuser 116 is disposed forward of the plurality of narrowband coloured light sources 114, in the path of emitted light, to ensure that the output of the array of LEDs is evenly mixed before the emitted light reaches the target 110. In this way, a reliable measurement of the measurable values of the coloured light which provides an improvement of the subject's perception of tinnitus may be achieved. Diffuser 116 may be any light scattering media which comprises a material capable of changes in the refractive index over short distances to provide effective mixing of the array of LEDs, such as a lenticular screen or a microlens array.

Optionally, divergence lens 108 may be provided, disposed forward of the colour controllable light source 106, in the path of the emitted light. The provision of a divergence lens 108 extends the effective area of illumination on the display 110 such that a greater area is illuminated during the assessment. A suitable divergence lens 108 is a conventional meniscus lens or a compact equivalent such as a Fresnel lens.

Display 110, which is illuminated by the apparatus 100 of the present invention, may suitably be the internal surface of a wall of a darkened, soundproof room in which the subject is placed.

Figure 2:
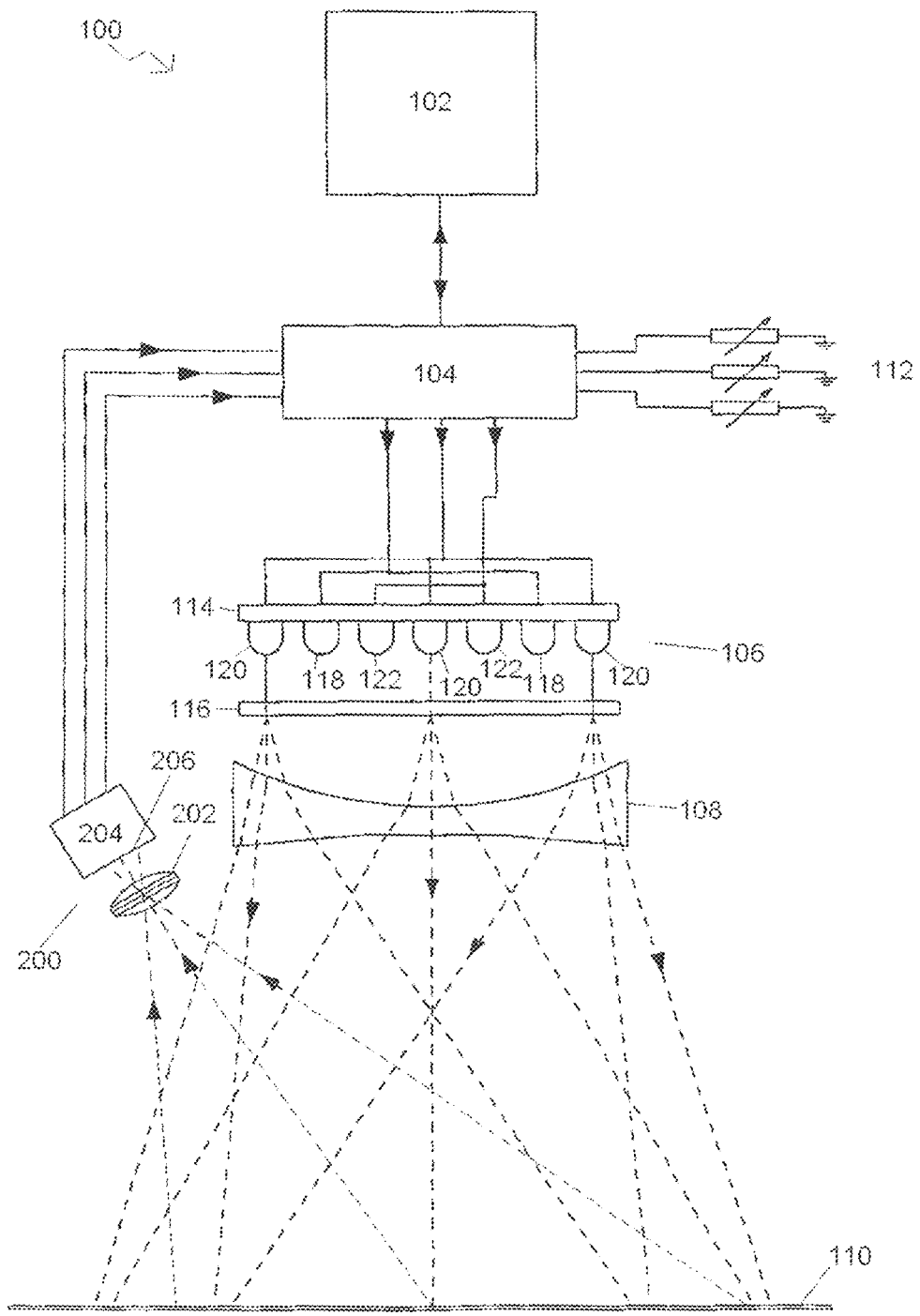
FIG. 2 is a schematic representation of apparatus suitable for use in a second embodiment of the method of the present invention.

With reference to FIG. 2, there is shown identical apparatus to the apparatus of FIG. 1. Accordingly, identical reference numerals used in FIG. 2 correspond to those used in FIG. 1, as described above. However, the apparatus 100 as shown in FIG. 2 is suitable for use in the method of assessing the effect of coloured light a subject's perception of tinnitus wherein the measurable values are tristimulus values. Accordingly, the apparatus 100 comprises a camera assembly 200, which is configured to account for ambient light and so allow the computer 102 to determine what the tristimulus values of the light entering the subject's eye will be.

Camera assembly 200 comprises a lens 202 and a camera 204 having a receiving surface 206. In use, lens 202 forms an image of the light reflected from display 110 on the receiving surface 206 of the camera 204. Camera 204 may be a CCD or other photo-detector array and receiving surface 206 thereof may be a colour filter array. Camera 204 is connected to the computer 102 to relay the image of the reflected light to the computer 102 for analysis. Using known techniques, the video signal from the camera 204 can be analysed by the computer 102 to establish the level of illumination at display 110 and its colour mix. Light passing through the colour filter array of the receiving surface 206 can be translated by the computer 102 using a specific matrix, into a red, green and blue LED light combination. From this data, the computer 102 can calculate the tristimulus values of the coloured light using known techniques and so define coordinates of the coloured light for illustration in a chromaticity diagram from the relevant tristimulus values by methods well-established in the art.

As will be appreciated, the control unit 104, the colour controllable light source 106 and the diffuser 116 of FIG. 1 or the control unit 104, the colour controllable light source 106, diffuser 116 and camera assembly 200 or FIG. 2 may alternatively be incorporated into single device such as a computer, laptop or like.

Figure 3:
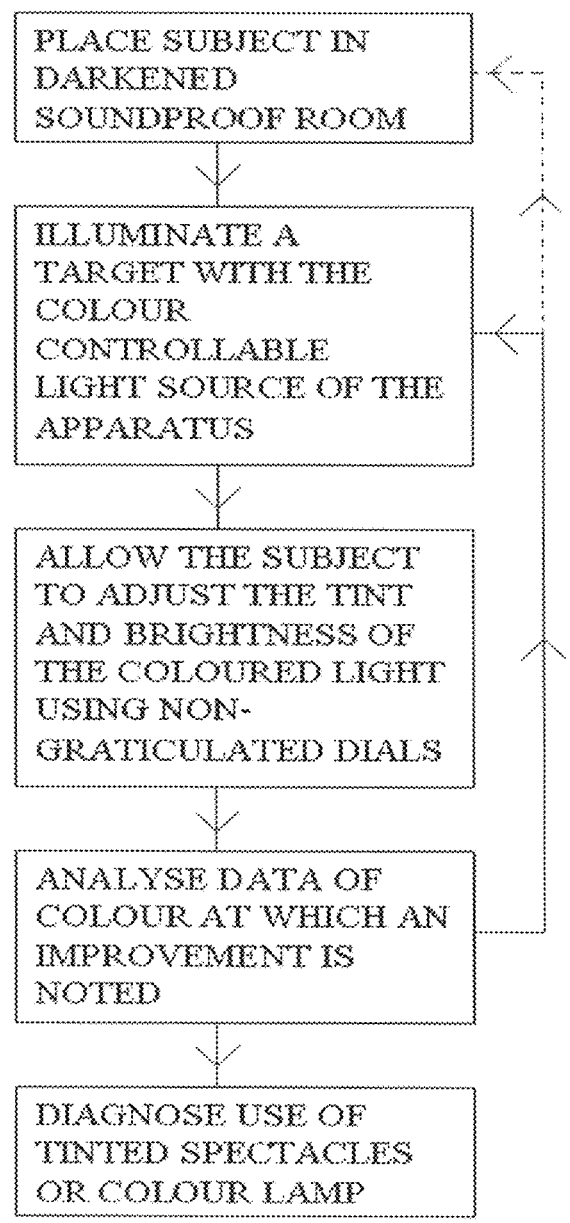
FIG. 3 illustrates a flowchart providing the preferred method of assessing the effect of light on a subject's tinnitus in accordance with one embodiment of the present invention.

Use of the apparatus of FIG. 1 and/or of FIG. 2 will now be discussed with reference to FIG. 3 which shows a preferred method for assessing a subject's perception of tinnitus.

To set up the instrument ready for use, the control unit 104, colour controllable light source 106 and divergence lens 108 of the apparatus 100 is placed in a suitable environment of low luminance and low background noise level and arranged such that in use, light emitted from the colour controllable light source 106 will illuminate a suitably positioned white, flat surface that does not interfere with the emitted coloured light. Meanwhile, the computer 102 is located remotely of the rest of the apparatus 100, with a trained clinician. In this way, diagnosis may be undertaken by the trained clinician and not the subject themselves.

The subject is then placed in the suitable environment with the control unit 104, colour controllable light source 106 and divergence lens 108 of the apparatus 100. The subject is positioned such that they can easily access and control to the non-graticulated dials of the control unit 104 and are facing the display 110 to be illuminated by the colour controllable light source 106.

The subject is allowed to acclimatise to the environment for 30 seconds, after which apparatus 100 is switched on to illuminate the display 110 with the colour controllable light source 106. The subject can then vary the amounts of red, blue and green light present in the light projected by colour controllable light source 106 by adjusting the non-graticulated dials at will. The subject indicates when the coloured light projected onto the display 110 is perceived to have a positive effect on their perception of tinnitus, for example an improvement. The measurable values of the coloured light perceived to provide the positive effect are recorded on the computer 102. Where the apparatus 100 comprises the camera assembly 200 of FIG. 2, the video signal obtained by the camera assembly 200 is simultaneously recorded on the computer 102 and both data sets are analysed to give the tristimulus valves of the light, which is plotted on a CIE chromaticity diagram. This data is then stored on the computer 102 for future use.

To ensure reliability of the results, the colour controllable light source is reset by the trained clinician resetting of the measurable values of the coloured light using the computer 102. The subject then repeats the process described above until they perceive a positive change in their tinnitus. As in the previous process, the data of the coloured light is analysed and recorded on the computer 102. The result of the second test may provide an improvement at either the same point in colour space as the previous test or a different point, in which case the subject will be exposed to each of the preferred measurable values of the coloured light so that they may select which has the optimal effect on their perception of tinnitus.

The subject may further undergo the process at any later time, to establish re-test variability of the response.

Once an optimum colour tint has been identified by the above process, the trained clinician can then diagnose the use of one or more of the articles described above to help alleviate the perception of tinnitus. For example, the clinician may diagnose use of tinted spectacles, which will be fitted with a filter adapted to absorb all other components of light, whilst allowing coloured light having the tristimulus values found by the above procedure to pass therethrough. Alternatively or additionally, the clinician may diagnose use of a coloured light source, wherein the light source is a suitably calibrated light source fitted with a similar filter as described above or it can be adapted to emit coloured light having the mixture of wavelengths and/or tristimulus values associated with the coloured light determined by the above process.

Experiment 1: Responses to Random Colour Presentation Method

In this set of experiments, 94 subjects clinically assessed as presenting with chronic tinnitus were asked to report if their tinnitus was affected by the three single light colours changed at random by the subject. This was done by first demonstrating the use of the three non-graticulated dials of the apparatus of the present invention. They were allowed to familiarise themselves with the operating dials. They were then instructed to inform the experimenters when they perceived any change in their tinnitus.

After practice the lights were turned off and the subjects were allowed to acclimatise to the dark for 30 seconds. They then changed the dials at will until they reported a change in tinnitus perception, i.e. an improvement or a worsening, as judged by a perceived decrease or increase in the intensity level or a change in pitch. The X:Y colour co-ordinates of the coloured light at which a change was perceived were recorded by the computer and the co-ordinates were reset randomly away from these X:Y colour co-ordinates by the experimenter.

The subject then repeated the process at least once until they again experienced a change in their tinnitus. In some cases, they reported more than one point in colour space associated with changes in their tinnitus perception. In this case they were asked to select the one that appeared to be optimal for them. The X:Y values were recorded again by the computer.

Results

Table 1 shows that out of 94 subjects, 41/94 or 44% reported an improvement in their tinnitus with one or more points in colour space, with 6/94 or about 6% reporting a worsening. Overall, 50% reported a change in tinnitus perception. Review of the descriptions of a change in tinnitus were based on either it was considered an improvement or worsening.

TABLE 1

Proportion reporting an effect with Random Colour

| CATEGORY | N | Percentage |
|---|---|---|
| Worse | 6 | 6% |
| Same | 47 | 50% |
| Improved | 41 | 44% |

Changes in Mood

One of the possible confounders to the study was that many subjects reported that the light as presented was considered 'soothing' and it was possible that this was affecting the report of the effect of the light on tinnitus. To establish whether there was any relationship with reports of 'soothing effects' with a change in tinnitus, Table 2 was drawn up. This shows that there is no evident relationship between reports of a 'soothing effect' and reporting an improvement in tinnitus, with a 15% association between the two. This compares with about 50% of those who also reported 'no effect' on tinnitus as reporting a random colour as soothing.

TABLE 2

Proportion reporting non auditory soothing effect with Random Colour

| Response: Effect on tinnitus | Soothing Effect Reported | No Soothing Effect Reported | % Reporting Soothing | Fisher's Exact p |
|---|---|---|---|---|
| Worse | 0 | 6 | 0% | |
| No Effect | 24 | 23 | 51% | |
| Improved | 6 | 35 | 15% | 0.002 |

Figure 4A:
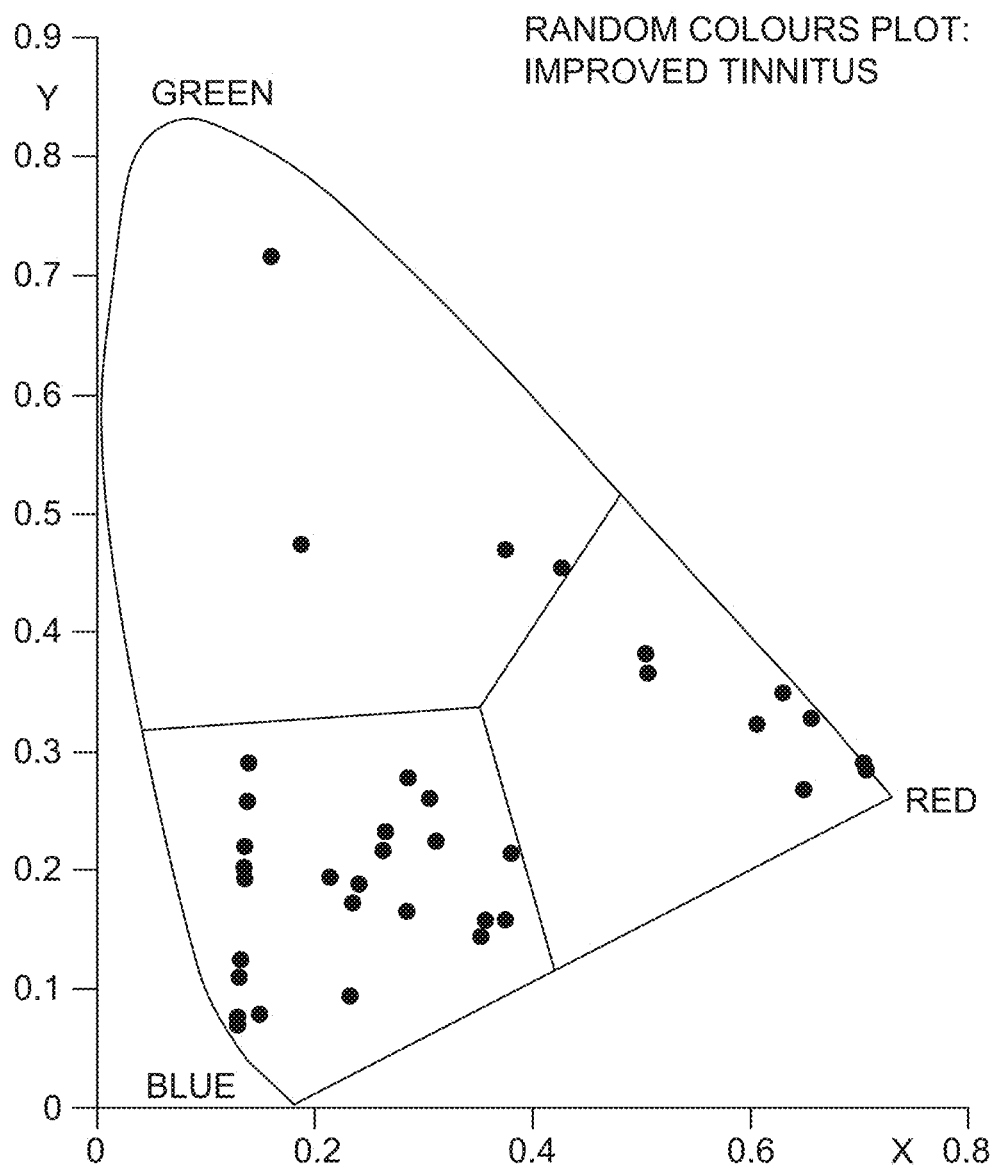
FIG. 4a is a graphical representation of a chromaticity diagram with random colour plots for the subjects experiencing an improvement in their tinnitus and FIG. 4b shows a comparative representation of a chromaticity diagram with the associated wavelengths illustrated thereon.
Figure 4B:
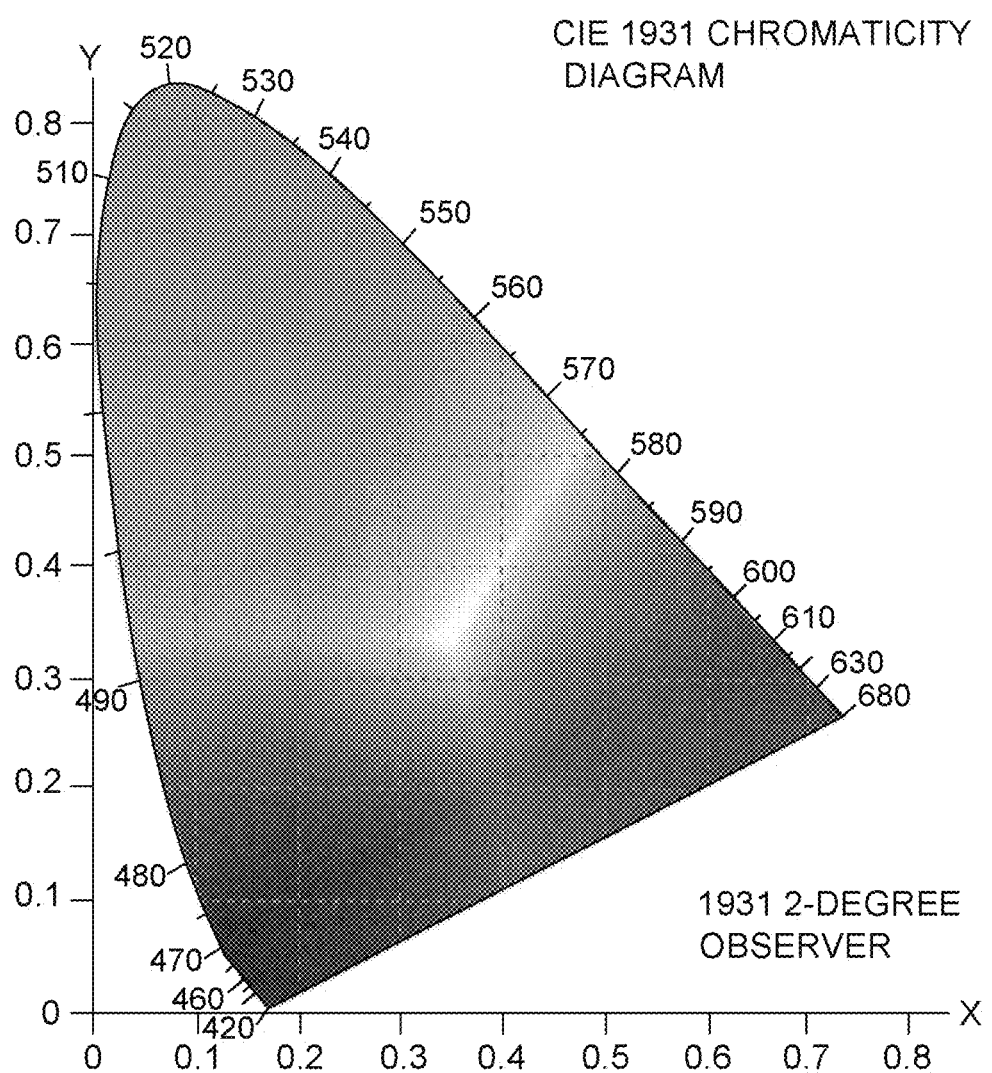

Experiment 2: Random Colour Choice—Distribution in Colour Space
Random Colour: Improved Tinnitus Reports When individual frequencies on experiment 1 are plotted in colour space there was a clear preference for frequencies with a dominant blue component as shown in FIG. 4a. The accompanying CIE 1931 chromaticity (FIG. 4b) gives a comparative representation of colour space. In gross terms, of the 41 subjects who reported an improvement in their tinnitus, the proportions in the blue:red:green space are 29:8:4, or approximately 70%:20%:10%.

There is considerable scatter over the 'Blue' region of colour space, although a vertical 'line' of points is apparent at about CIE: 0.14-0.15. With 'Red', the eight values appear to be placed nearer the 'Red-Green' edge of the space. The four points in the 'Green' region do not have any apparent pattern.

This demonstrates that blue light is more generally associated with an improvement in a subject's perception of tinnitus. Whereas, the fact that points in the 'Red' region of colour space are placed near to the 'Red-Green' edge seem to suggest that substantially red tints are generally not associated with an improvement.

Experiment 3: Random Colour—The Effect of Light on Reported Improvements of Tinnitus, Repeatability and Variability I.

In those subjects reporting a response to tinnitus. investigation of two further important aspects of the apparent effect were possible, namely repeatability and variability of the reported effect. Both acute and longer term or chronic repeatability and variability were investigated and are considered separately in the following sections.

Reported Improvements in Tinnitus, Acute Repeatability and Variability.
Method

Of the forty one subjects reporting an improvement in their tinnitus, twenty three subjects went on to carry out acute repeats of the experiments as outlined above. Importantly again, apart from simple instruction on how to operate the non-graticulated dials, they received no additional direction from the observer and were asked to report when they experienced any changes in their tinnitus with a particular focus on any improvement. The interval between the two acute sessions was between at least 30 minutes and up to 90 minutes. During this period the subjects went outside the soundproof room and were able to relax and were not restricted in activities. They had not been asked to attempt to remember or review any aspect of their performance.

Given the great number of very fine gradations and variations (i.e. upper limit about $10^7$) in colour space, it was not expected that any clues as to their performance in choosing a highly specific colour point could have been at all remembered without specific information about dial settings.

Results

Figure 5A:
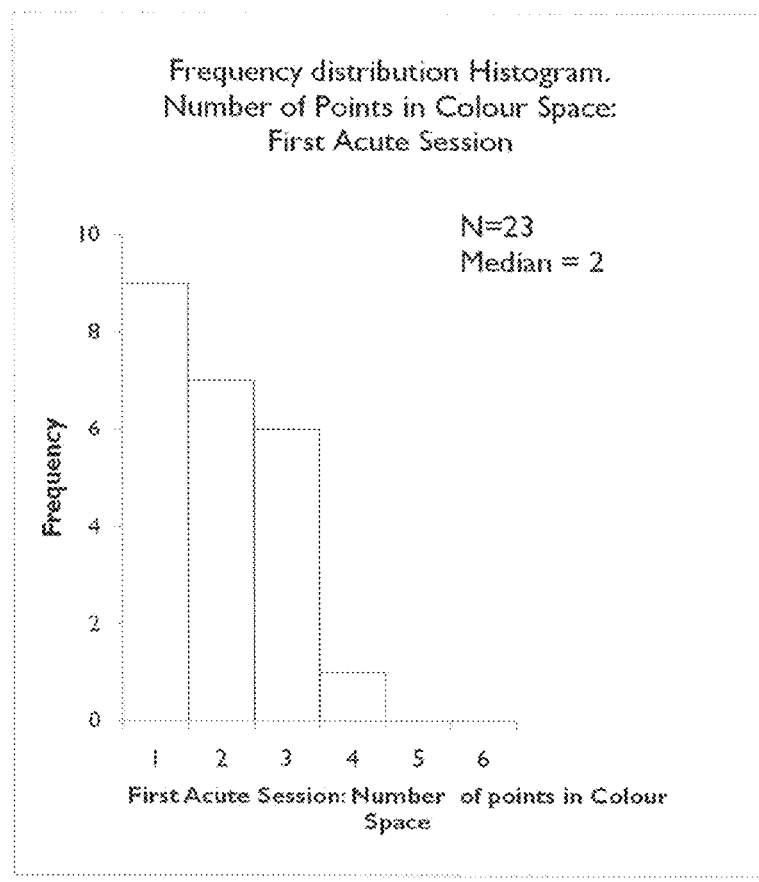
FIGS. 5a to 5d are graphical representations of the distribution of subjects identifying one or more points in colour space reported to improve tinnitus.
Figure 5B:
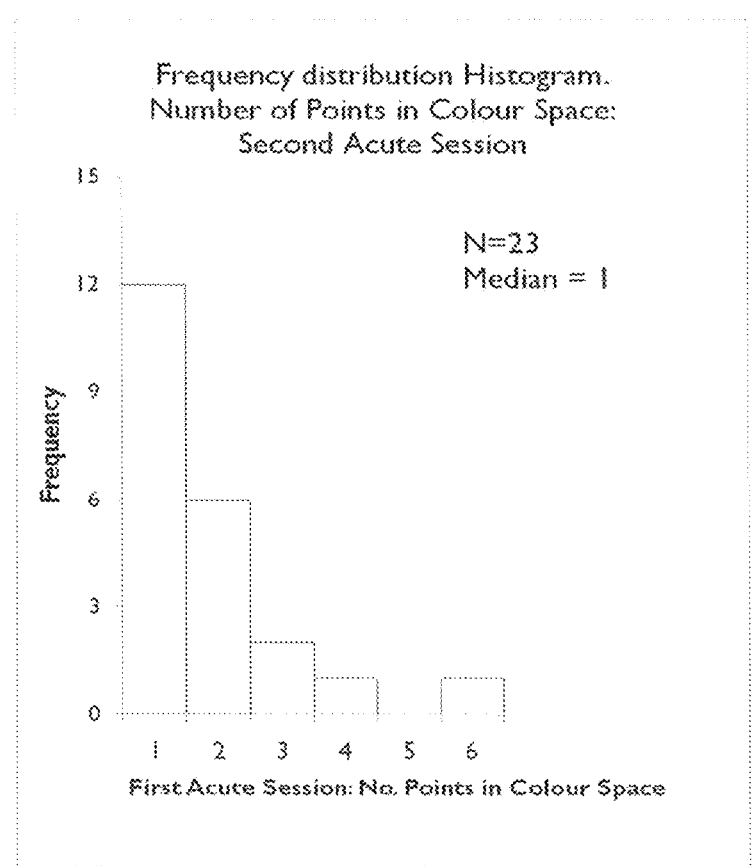

FIG. 5a shows that of the 23 subjects up to four points were chosen that were associated with reports of improved tinnitus with a median of two distinct points. FIG. 5b shows that in the second session, the number of points in colour space chosen had gone up to 6 in one subject although the median number of points had dropped to one. Overall, the number of points in colour space identified by individual subjects in the two tests was not significantly different.

Figure 5C:
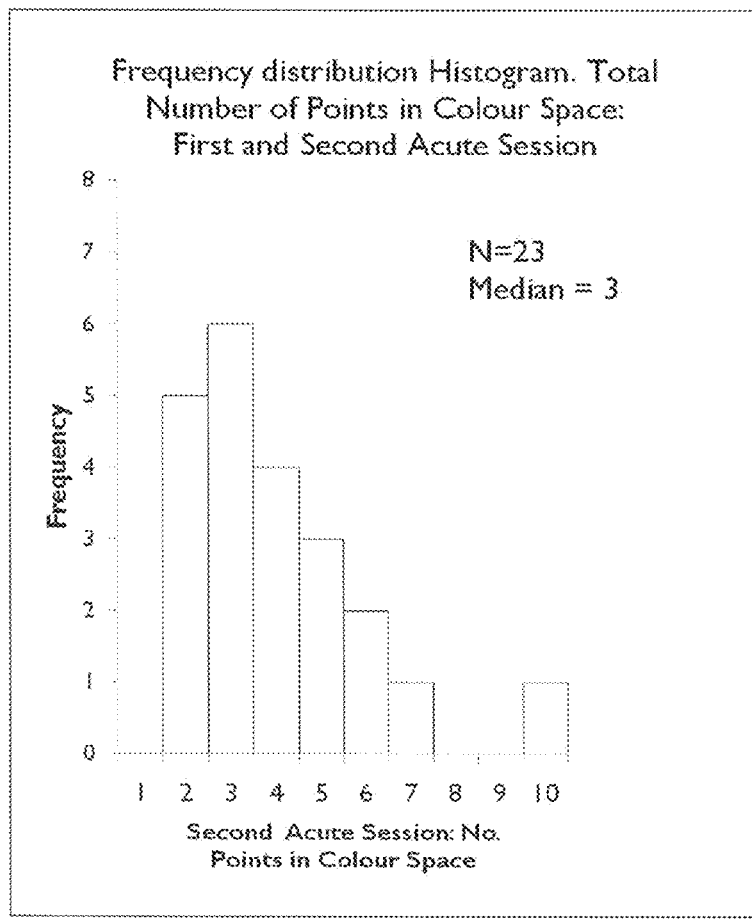

FIG. 5c shows the combined number of points, including repeated points of reported improvement over the two acute tests with a median of 3. These simple figures show that at least 50% of subjects reported that two or more points in colour space that appeared to improve their tinnitus. Biologically, this suggest that the phenomenon is not restricted the processing of a single colour and that therapeutics need not necessarily be limited to use of a single colour filter or generator.

Figure 5D:
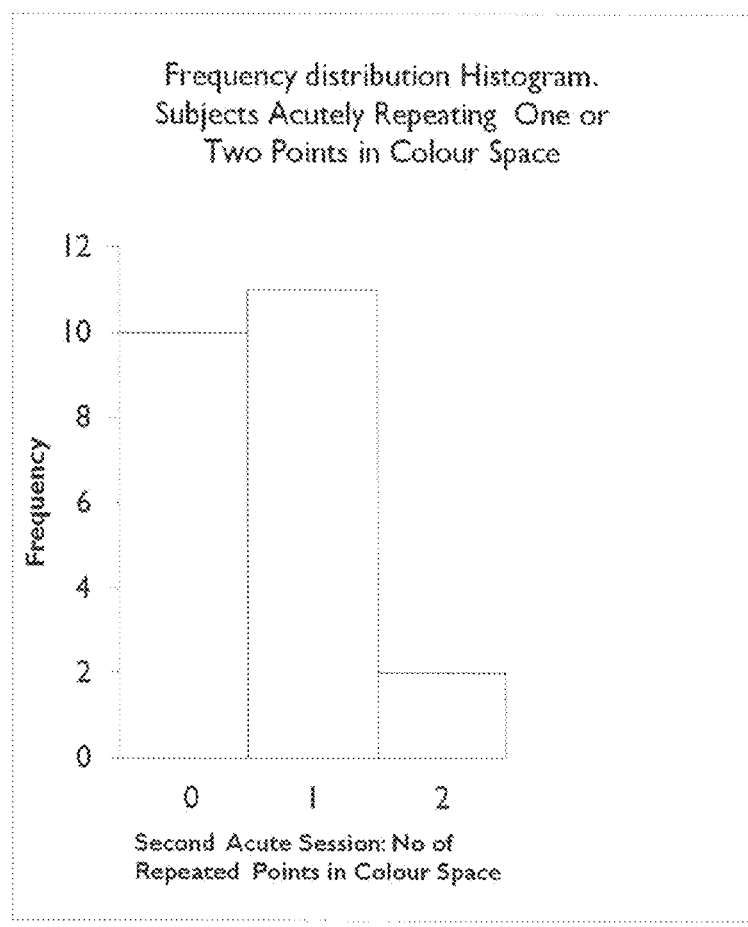

FIG. 5d shows that 13/21 (62%) of subjects independently repeating identical or very near identical point in colour space that reportedly improved their tinnitus. This finding is based on the central assumption that the subject is using improvement in their tinnitus to direct them back to a favoured point.

Individual Subject Repeatability and Variability

Figure 6:
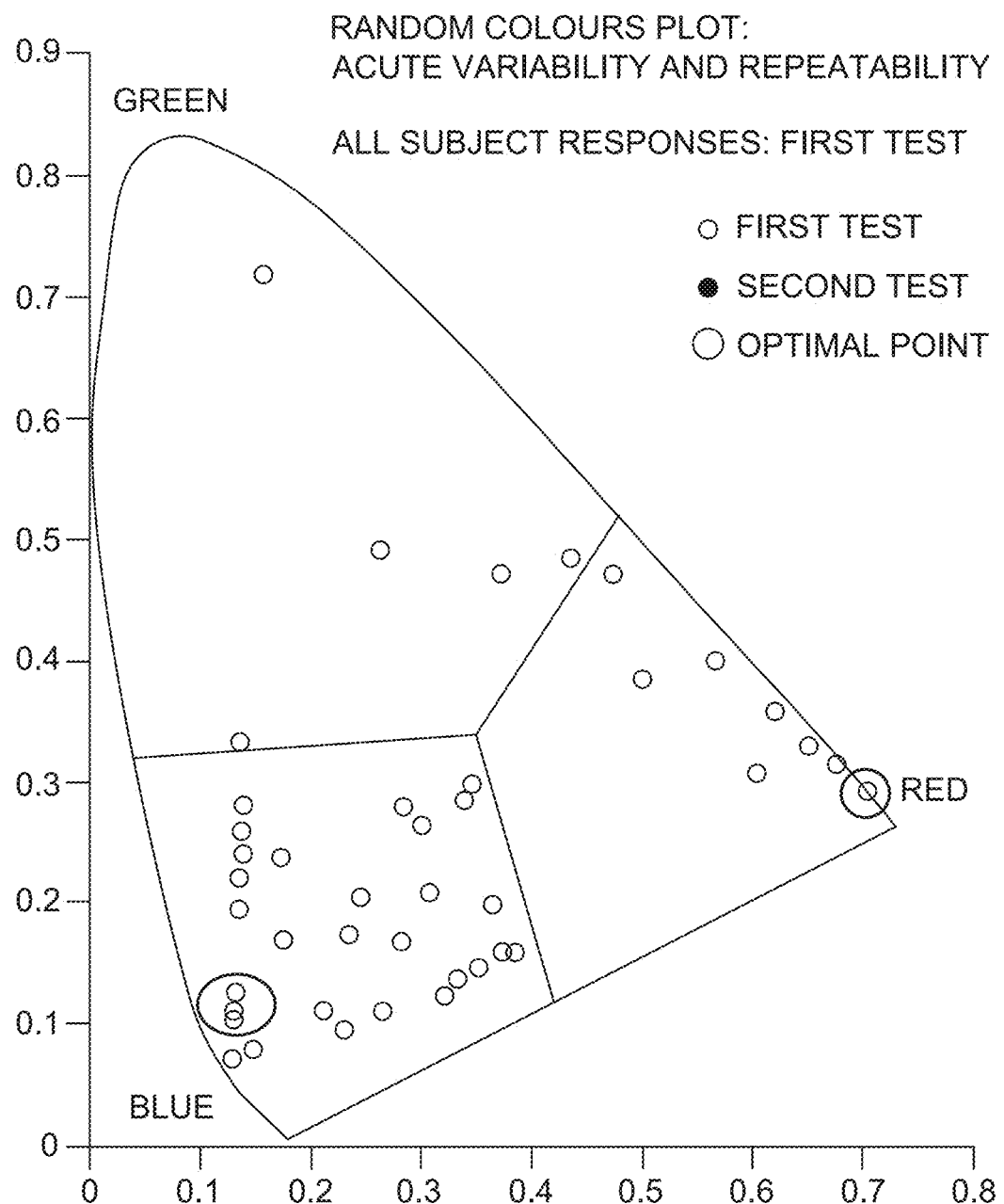
FIG. 6 is a graphical representation of a chromaticity diagram illustrating all colour points identified by all the subjects in the first test.
Figure 7:
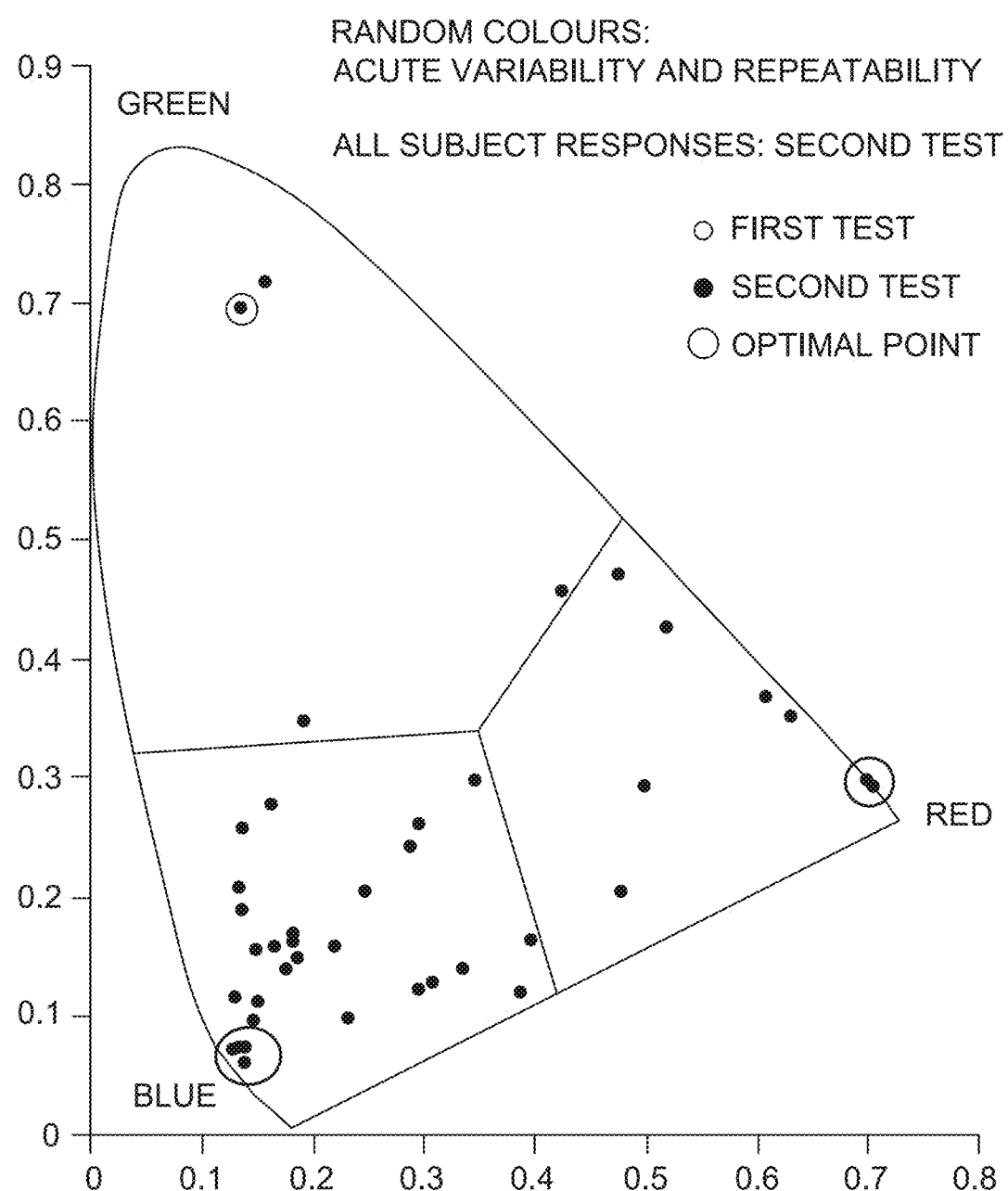
FIG. 7 is a graphical representation of a chromaticity diagram illustrating all colour points identified by all the subjects in the second test.
Figure 8:
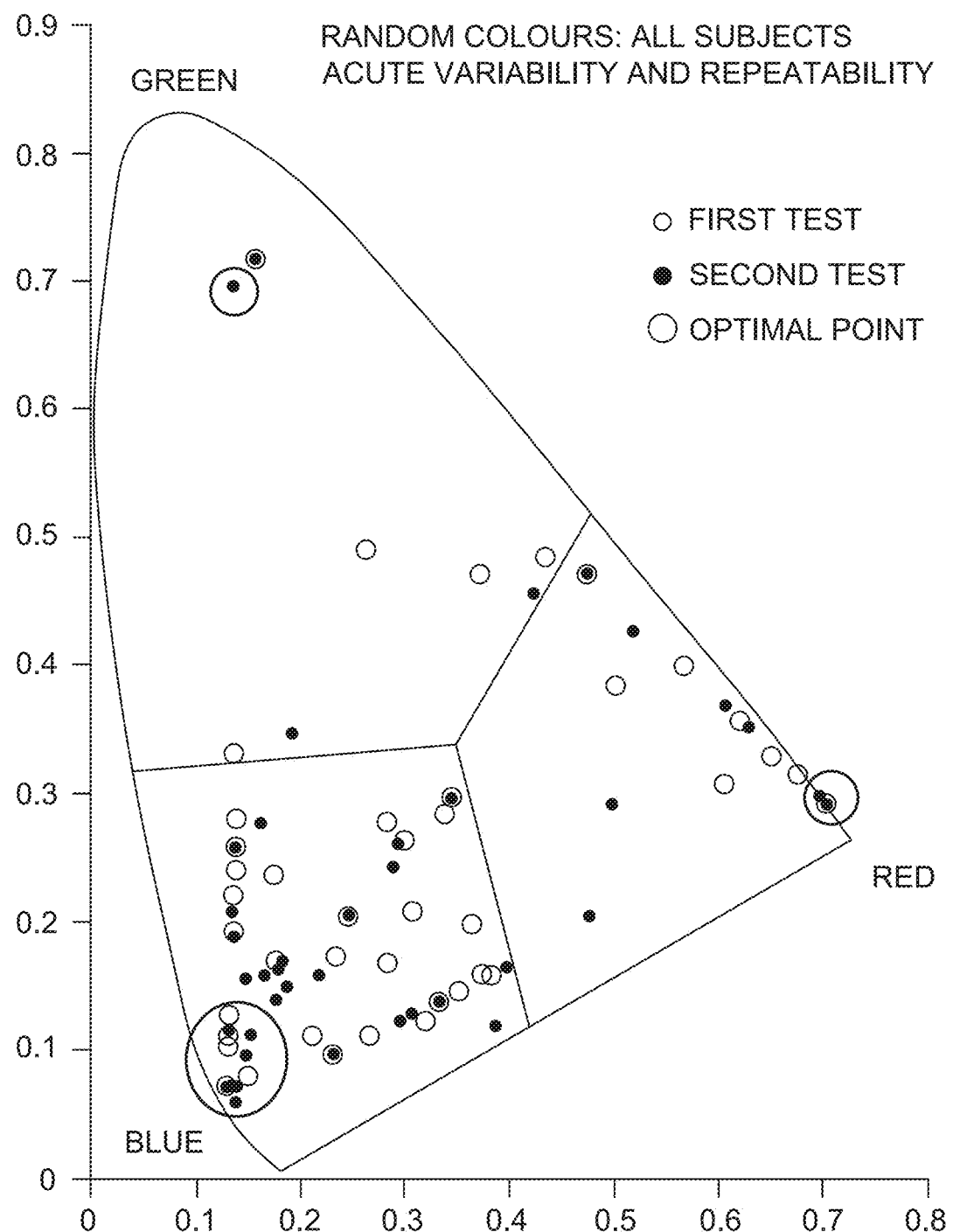
FIG. 8 is a graphical representation of a chromaticity diagram illustrating all colour points identified by all the subjects in both the first and second tests.

FIGS. 6 to 8 are scatter plots illustrating all points for the first, second and both tests respectively. These again illustrate the patterns as seen for the 41 subjects responding for a single optimal colour in FIG. 4a. FIG. 8 in particular graphically illustrates the repeatability observed in the acute study.

These figures also show the apparent emergence of a preferred optimal response points on the CIE plot, with this becoming more marked on FIG. 8. The most prominent is 'Blue' centred at about X:Y co-ordinates 0.15:0.1 (0.13:0.07 in the second acute test). At this point in FIG. 8, about 16/96 or 16% of all first and second test points lie.

Similarly for 'Red' a very clear preferred optimal response point centre on X:Y co-ordinates 0.706:0.294, with 8/94 or 8% of points lie. A 'Green' optimal response was less marked but two points independently arose within this portion of the colour space or about 2% of points.

Acute Repeatability and Variability in Colour Distribution

In gross terms, the 23 acute trial subjects generated a total of 47 and 49 responses in the first and second test respectively. A gross breakdown by the 'Blue' Red' and 'Green' regions of colour space are given in Table 3. This suggests that that the proportion of responses distributed over the three CIE colours boundaries are consistent over the acute test period of 30-90 minutes.

TABLE 3

Distribution of All Acute Responses by Colour Block and Test

| Acute Trial | Blue | Red | Green | Total |
|---|---|---|---|---|
| First Test | 30 (64%) | 10 (21%) | 7 (15%) | 47 |
| Second Test | 32 (65%) | 11 (23%) | 6 (12%) | 49 |

Experiment 4: Random Colour—The Effect of Light on Reported Improvements of Tinnitus, Repeatability and Variability II.

The number of subjects in the study enabled some preliminary investigation of chronic repeatability and variability of the reported effect. There was no set time period for repeatability but the time period between first and second testing in these experiments enabled broad inference to be made over a considerable time period of between 154-824 days, with a median of 272 days.

Reported Improvements in Tinnitus, Chronic Repeatability and Variability.
Method Of the forty one subjects reporting an improvement in their tinnitus, fifteen subjects went on to carry out chronic repeats of the experiments as outlined above. Importantly again, apart from simple instruction on how to operate the non-graticulated dials controlling Red, Green and Blue ('RGB') intensity, they received no additional direction from the observer and were asked to report when they experienced any changes in their tinnitus, particularly focusing on perception of any improvement.

Results

Figure 9A:
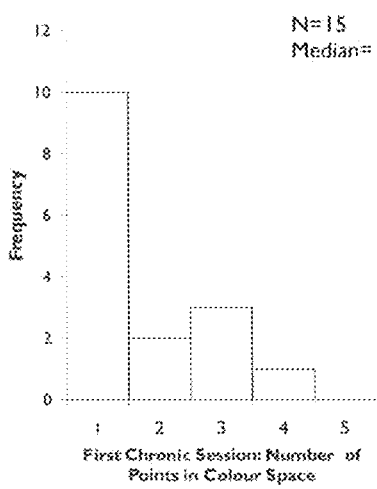
FIG. 9 are graphical representations of the distribution of subjects identifying one or more points in colour space reported to improve their tinnitus, in which 9a shows the first chronic test session, 9b shows the second chronic test session, 9c shows the first and second combined and 9d shows subjects repeatedly identifying the same one or two colour points.
Figure 9B:
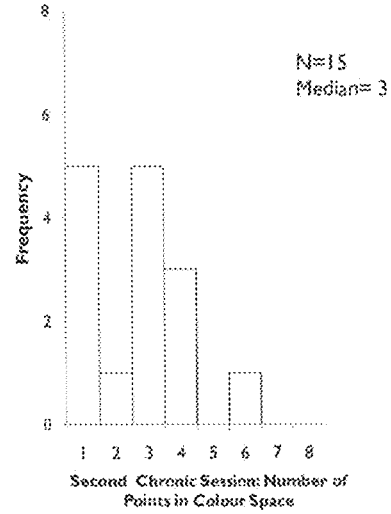

FIGS. 9a-d summarise the distribution of number of points reported for the first and second chronic test sessions. As with the acute tests, up to four points were chosen that were associated with reports of improved tinnitus with a median=1 point (FIG. 9a). These acute values include most of the data that formed the baseline for those who also performed acute tests. In FIG. 9b, the number of points reported to improve tinnitus was n=6 in one case with a group median of n=3. In the chronic tests, the difference in the number of points identified by individual subjects two tests was significantly different by Wilcoxon's Paired Sample Test (p=0.003).

As with the acute tests, both sets of results clearly indicate that more than one point in colour space can be associated with an apparent improvement in tinnitus.

Figure 9C:
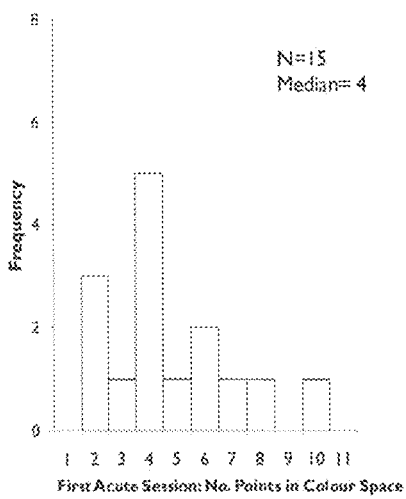

FIG. 9c shows the combined number of independent points, including repeated points of reported improvement over the two acute tests with a median of n=4. Again, as with the acute tests, at least 50% of subjects reported that two or more points appeared to improve their tinnitus.

Figure 9D:
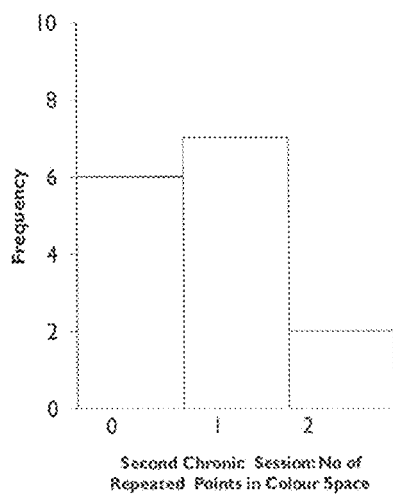

FIG. 9d shows that 9/15 (60%) of subjects were able to independently repeat an identical or very near identical point in colour space that reportedly improved their tinnitus for first and second testing. This percentage is comparable with the figure of about 55% for the acute testing.

Individual Subject Repeatability and Variability

Chronic testing subjects were further categorised as to their overall variability by the distribution of their points in colour space again not by specific CIE plot criteria, but by eye as to the overall closeness of number of points and repeatability. These were classified as exhibiting low, medium and high variability. The individual plots are shown in FIGS. 10a-f, FIGS. 11a-b and FIGS. 12a-g for each of these groups respectively.

The relative ratios of Low:Medium:High in the chronic subjects were 6:2:7 or about 40%:13%:47%. This is somewhat different to the ratios obtained for acute testing of 56%:13%:30%. Chronic repeatability was seen across all three groups.

Figure 10A:
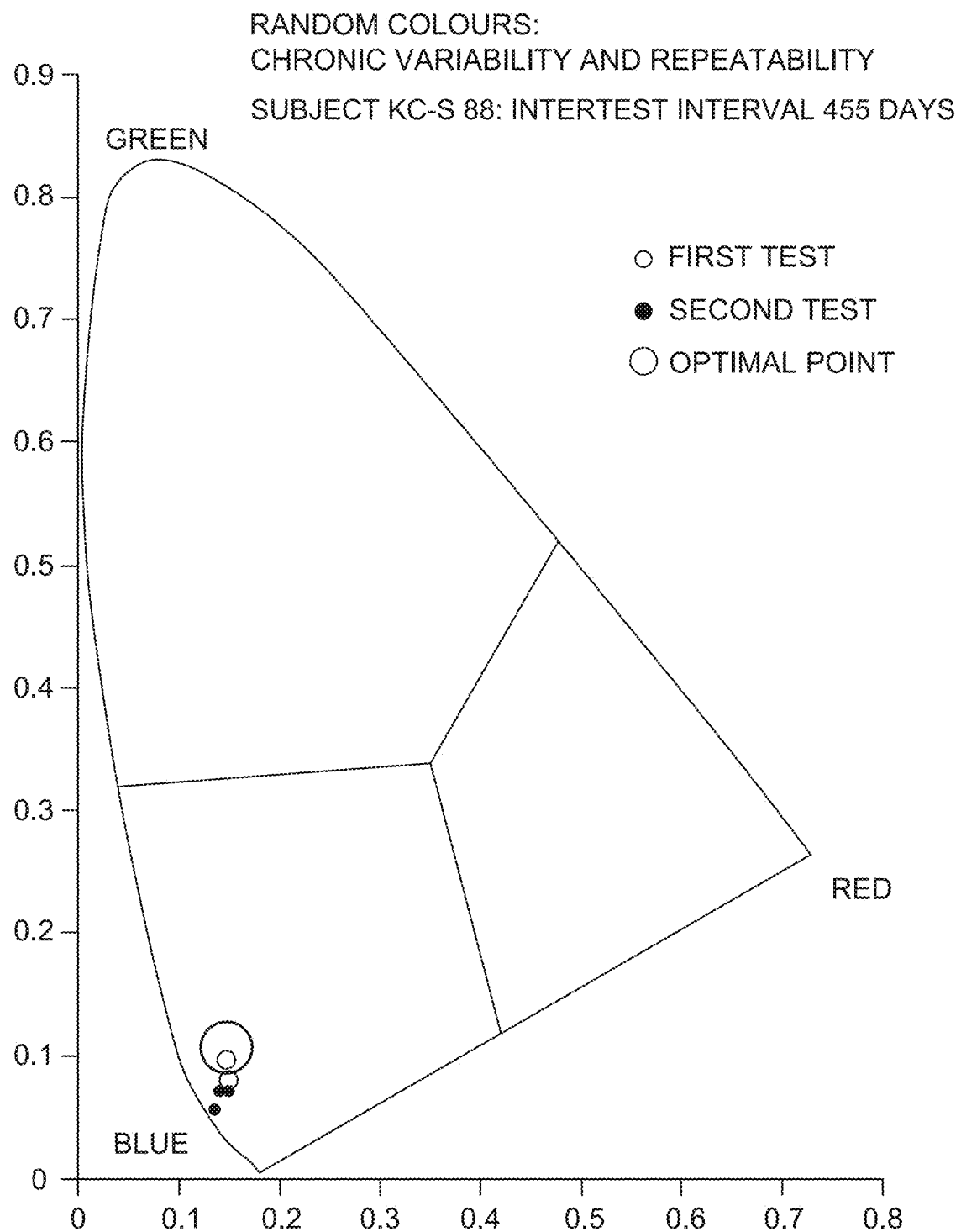
FIGS. 10a to 10f are graphical representations of chromaticity diagrams with chronic repeated individual subject's plots for an improved effect, categorised as having low overall variability.
Figure 10B:
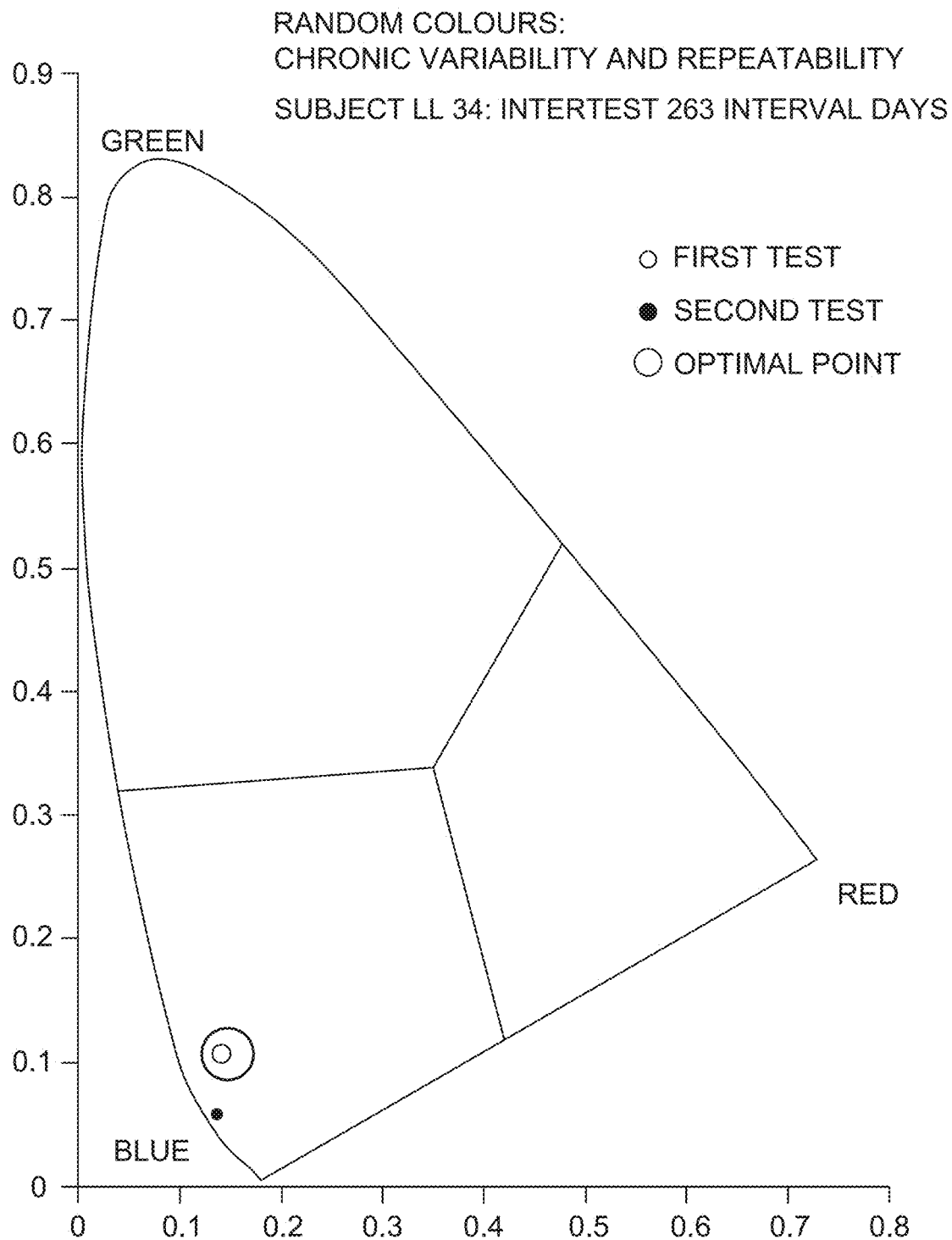
Figure 10C:
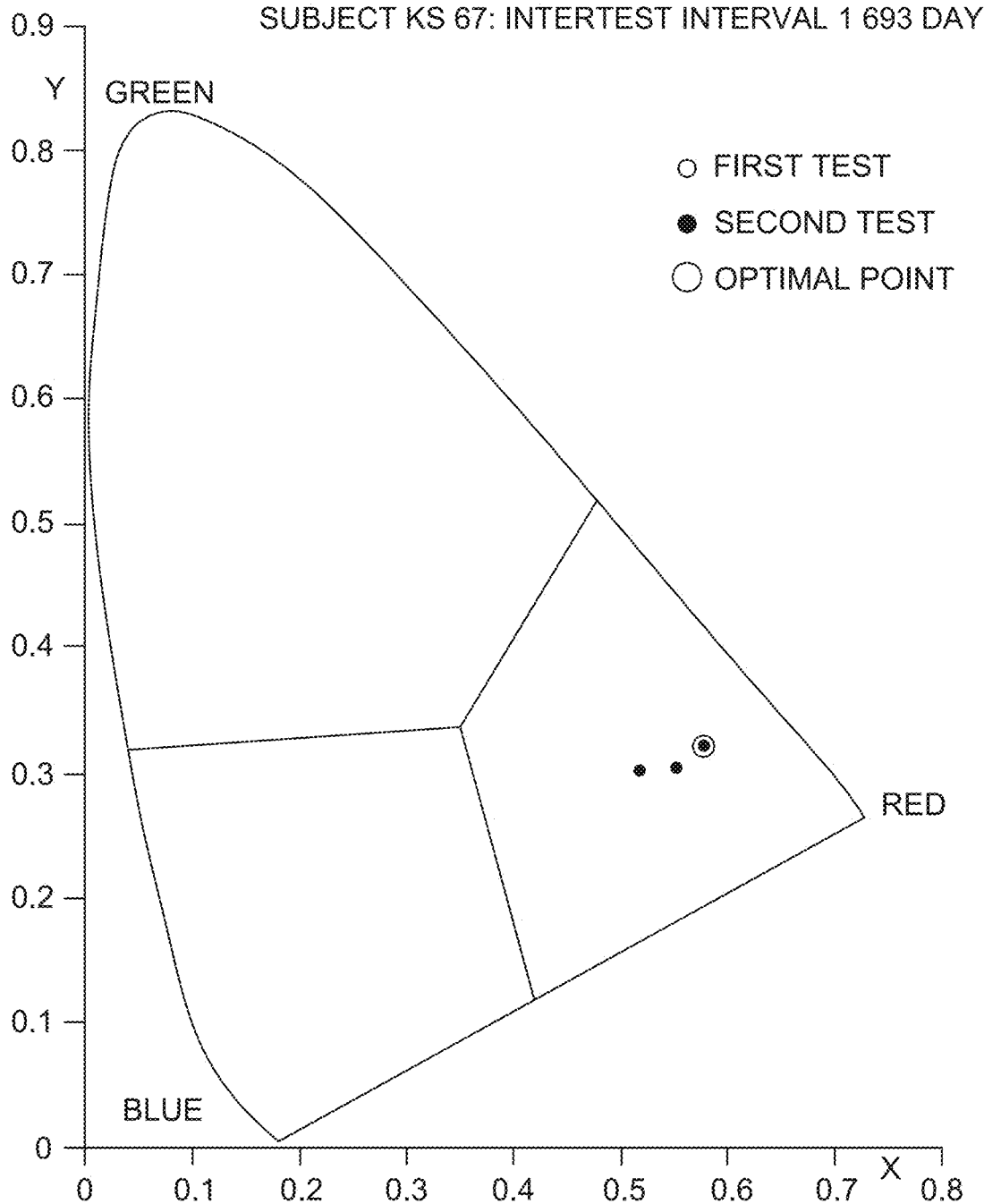
Figure 10D:
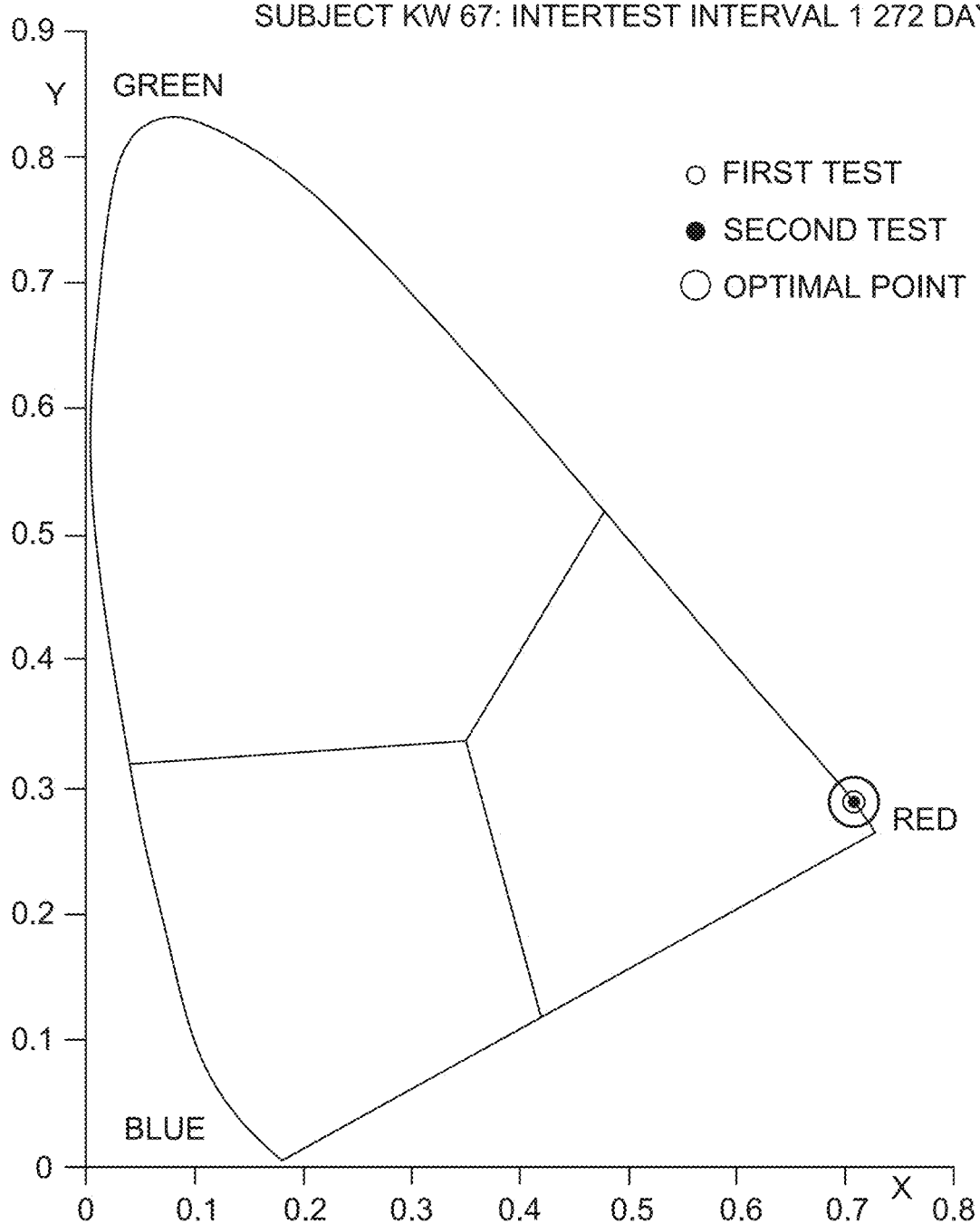

In the Low:Medium:High Variability Group, repeatability was seen in 4:2:3 subjects. These are seen in FIGS. 10a;c;d;e;f, FIGS. 11a;b and FIGS. 12a;e;f respectively. Notwithstanding the low numbers with merging of the Medium and High Groups, the proportions exhibiting repeatability are not significantly different between the Low and Medium-High groups.

Figure 10E:
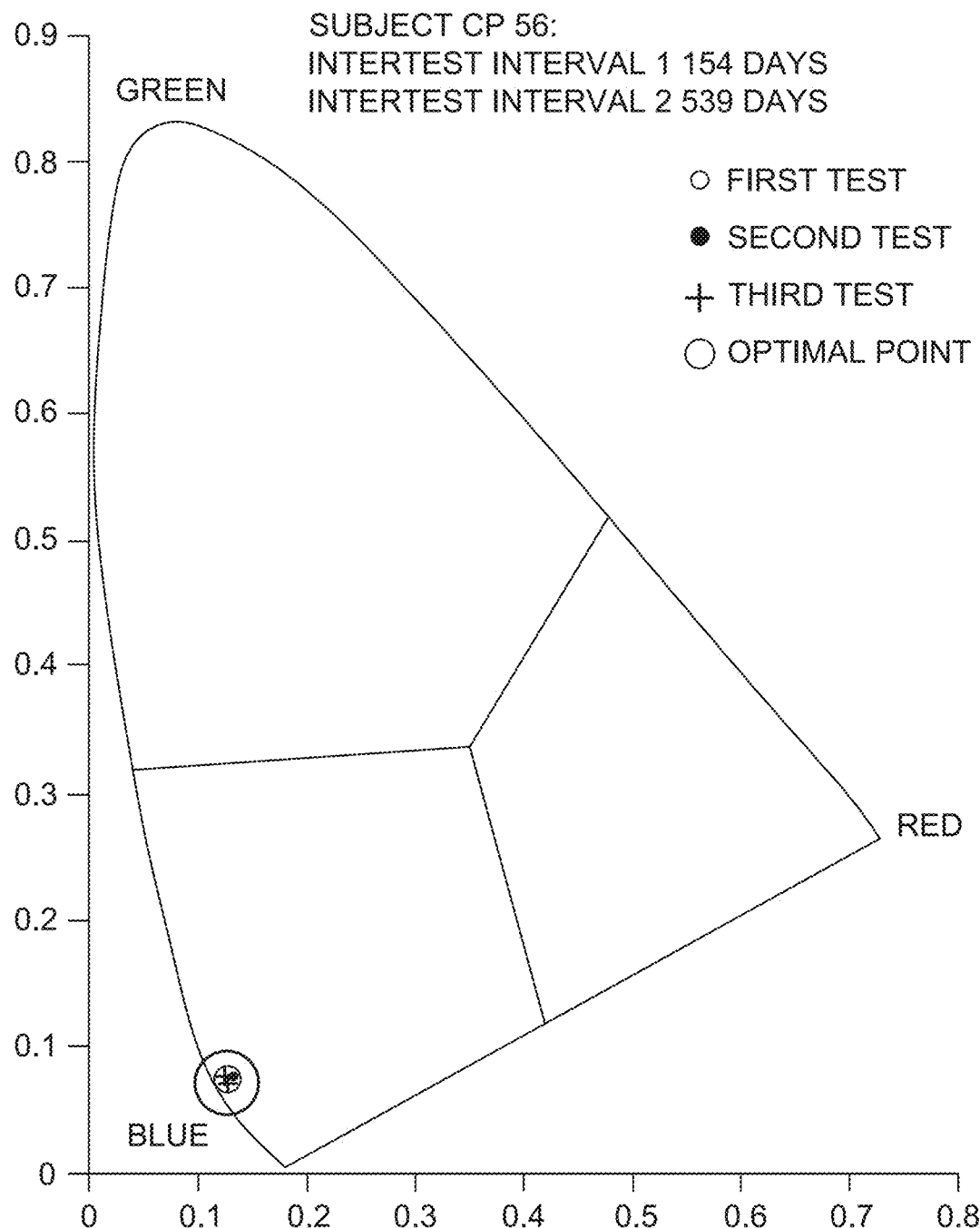
Figure 10F:
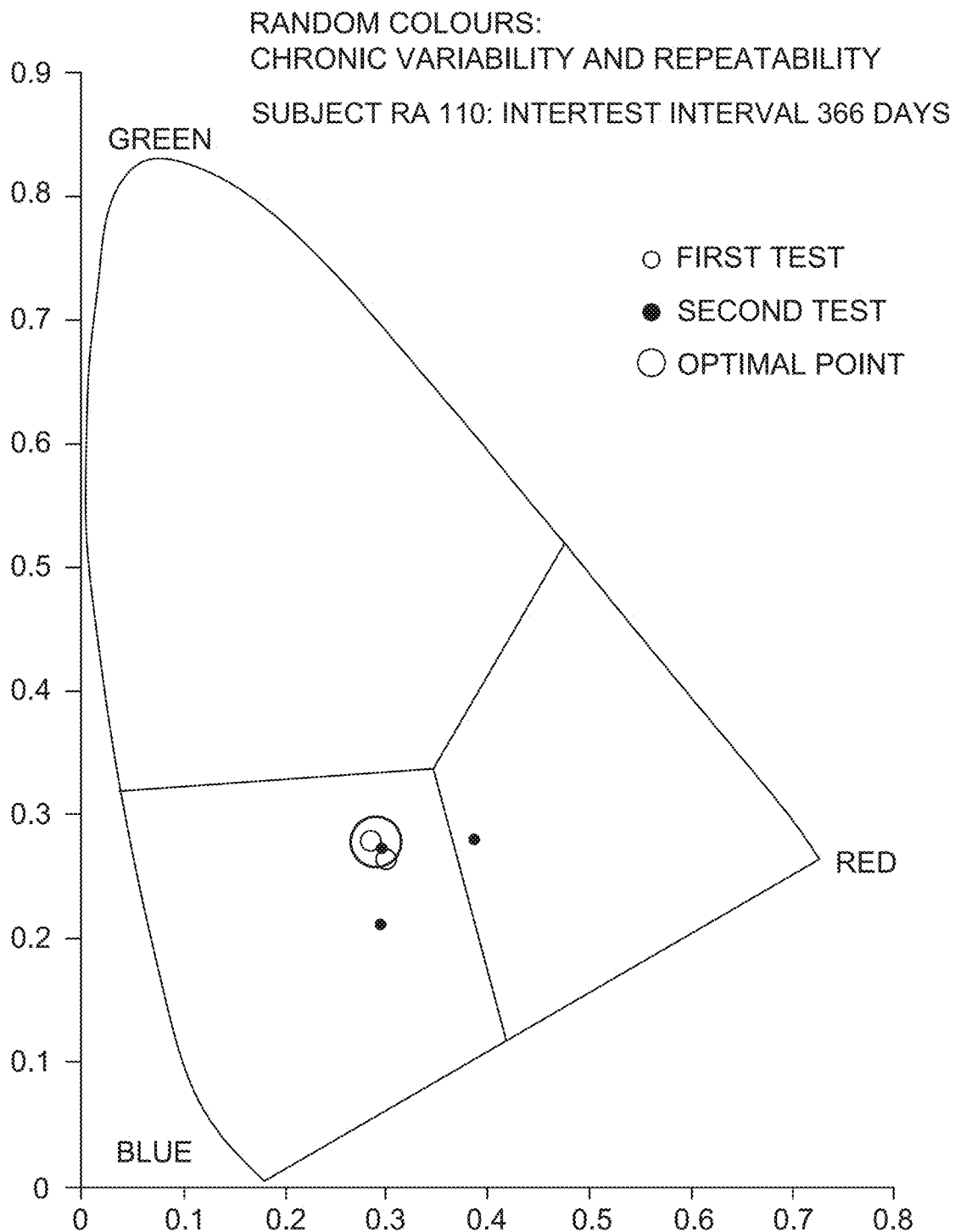
Figure 11A:
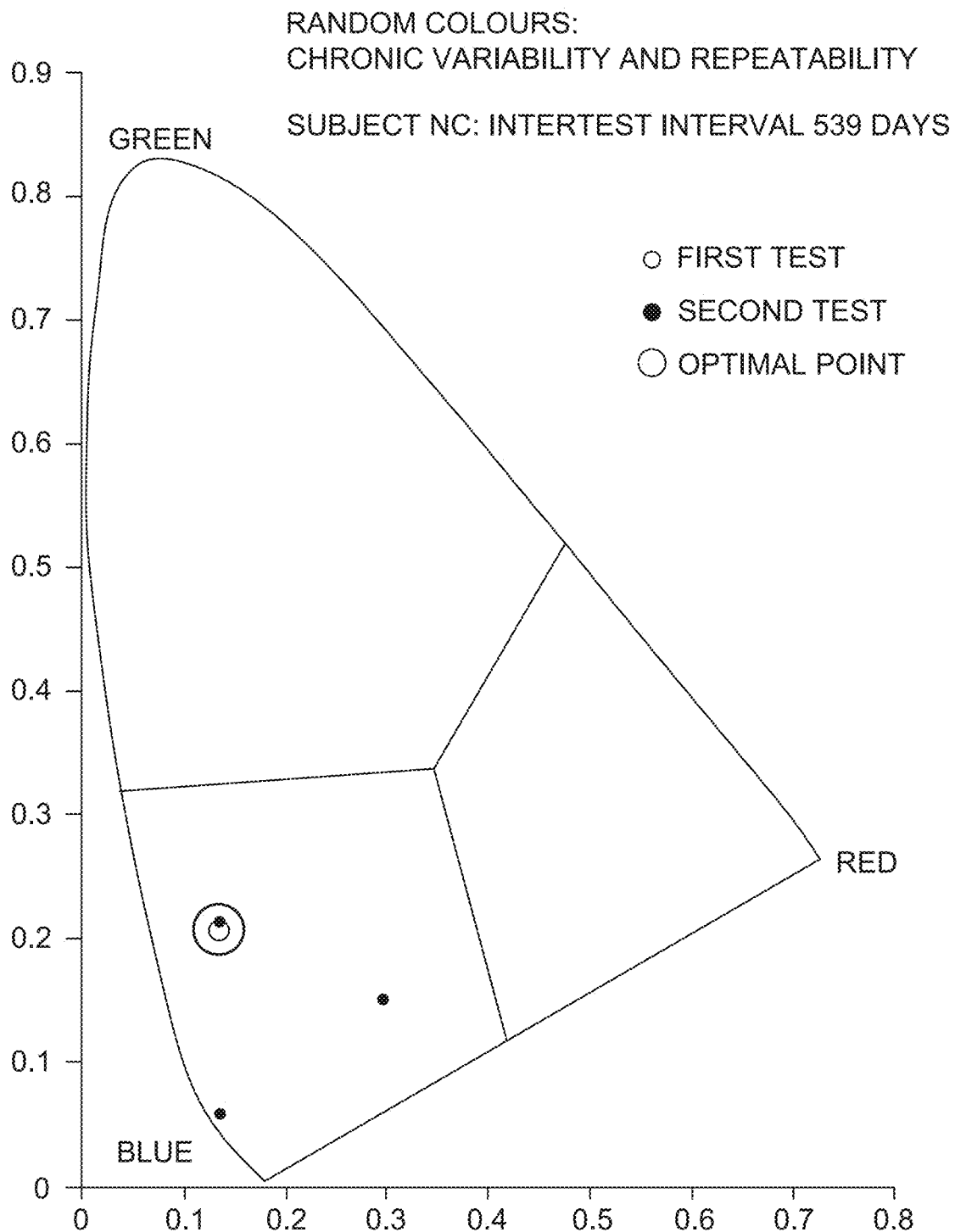
FIGS. 11a to 11b are graphical representations of chromaticity diagrams with chronic repeated individual subject's plots for an improved effect, categorised as having medium overall variability.
Figure 11B:
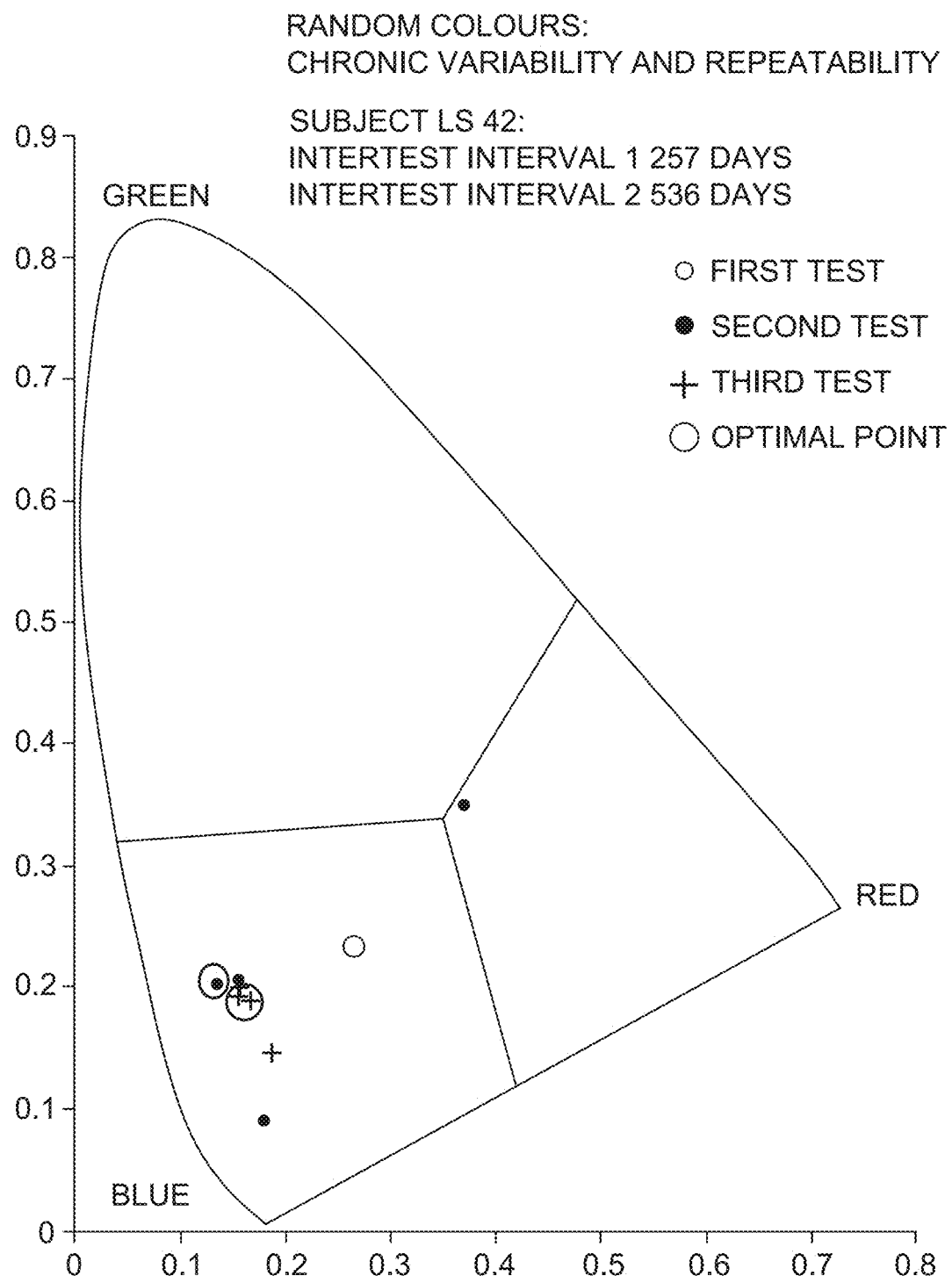
Figure 12A:
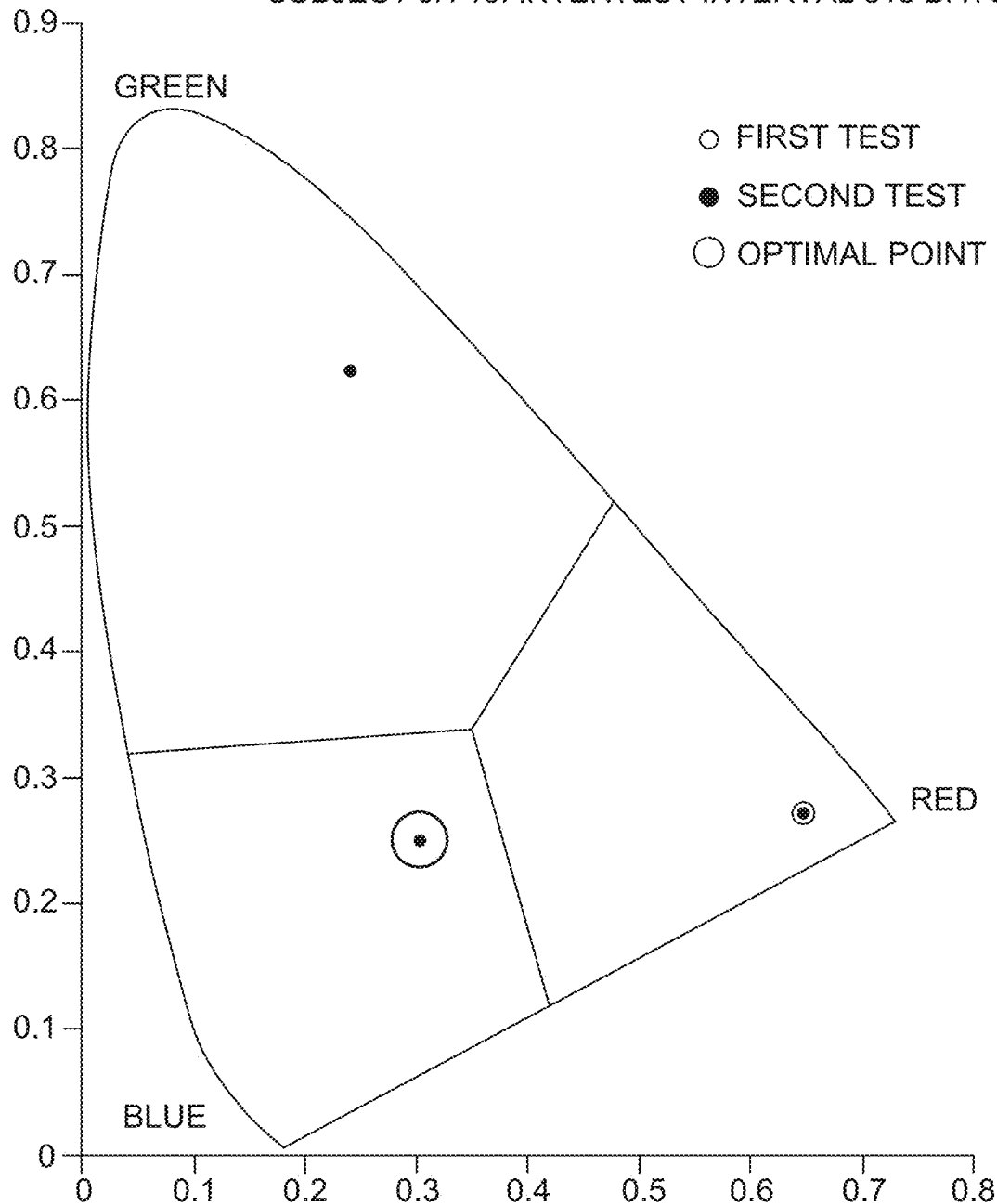
FIGS. 12a to 12g are graphical representations of chromaticity diagrams with chronic repeated individual subject's plots for an improved effect, categorised as having high overall variability.
Figure 12B:
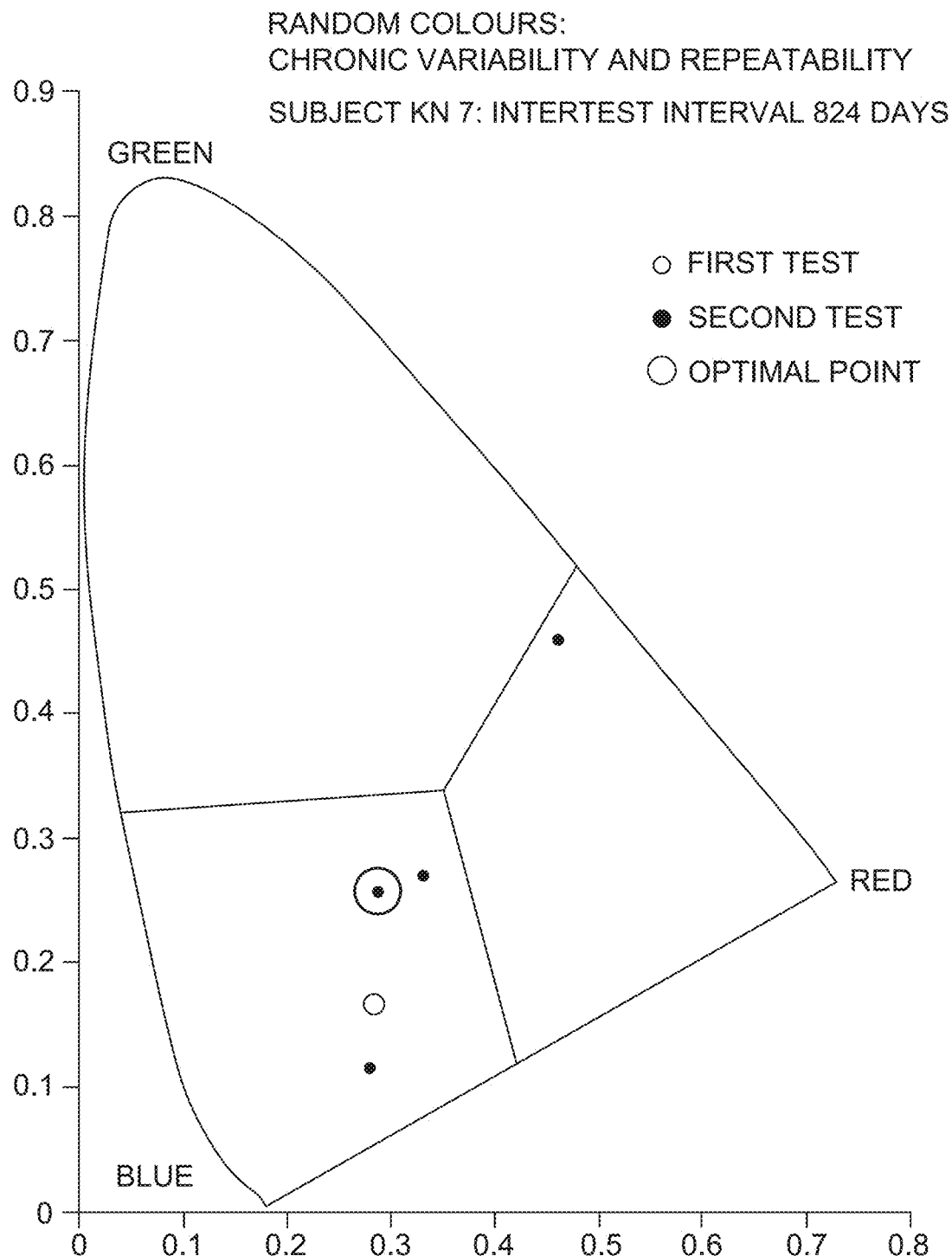
Figure 12C:
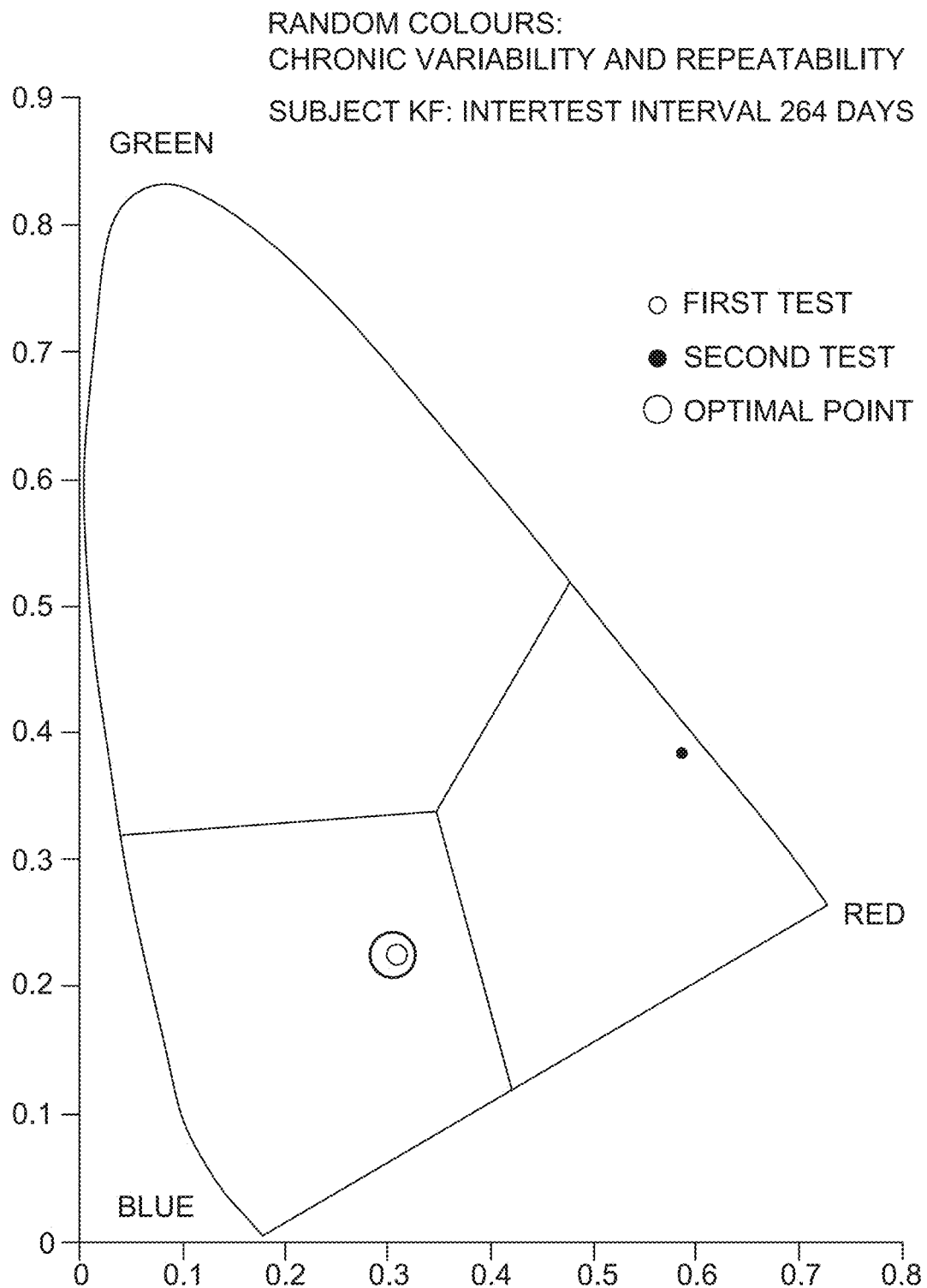
Figure 12D:
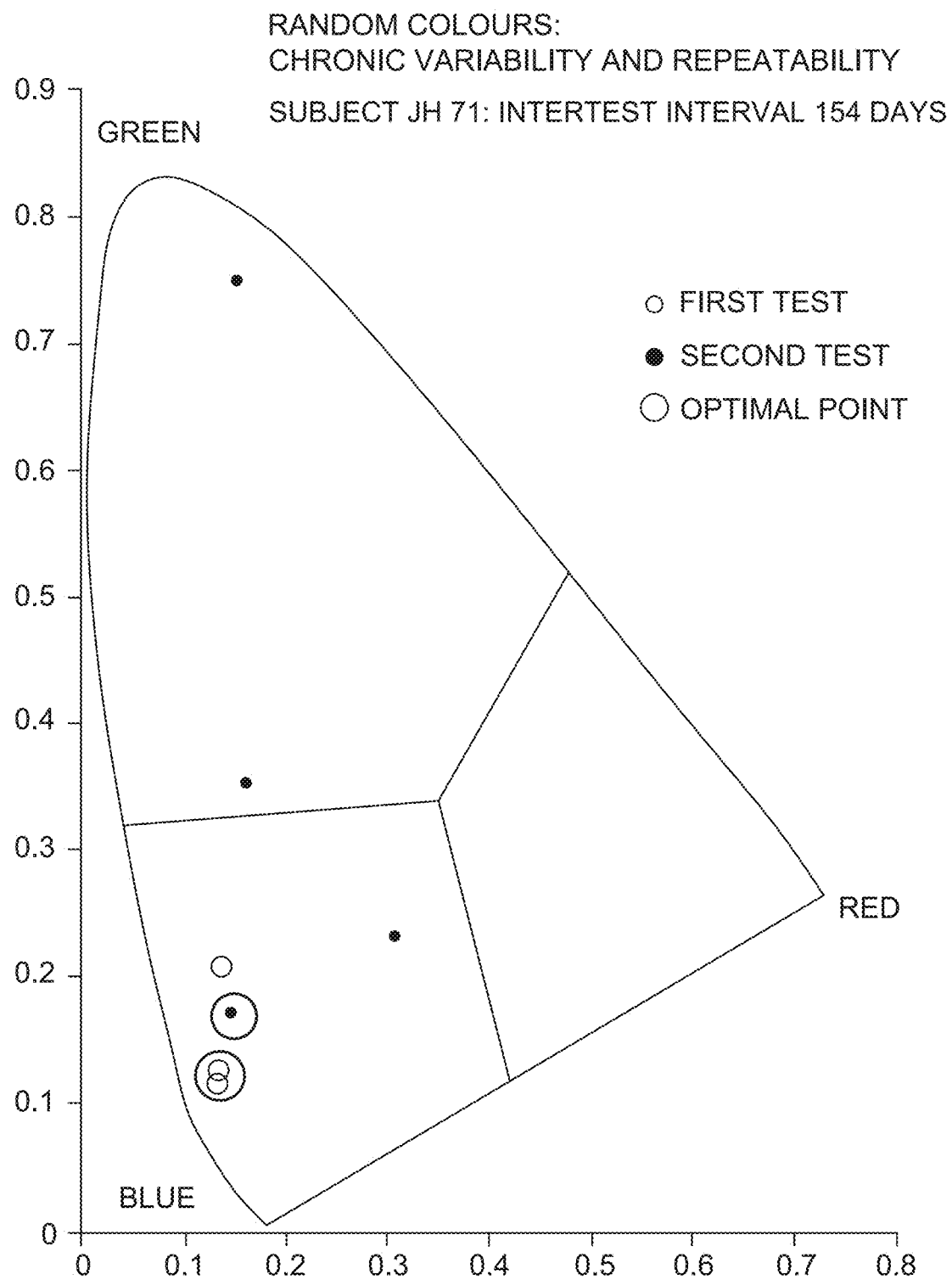
Figure 12E:
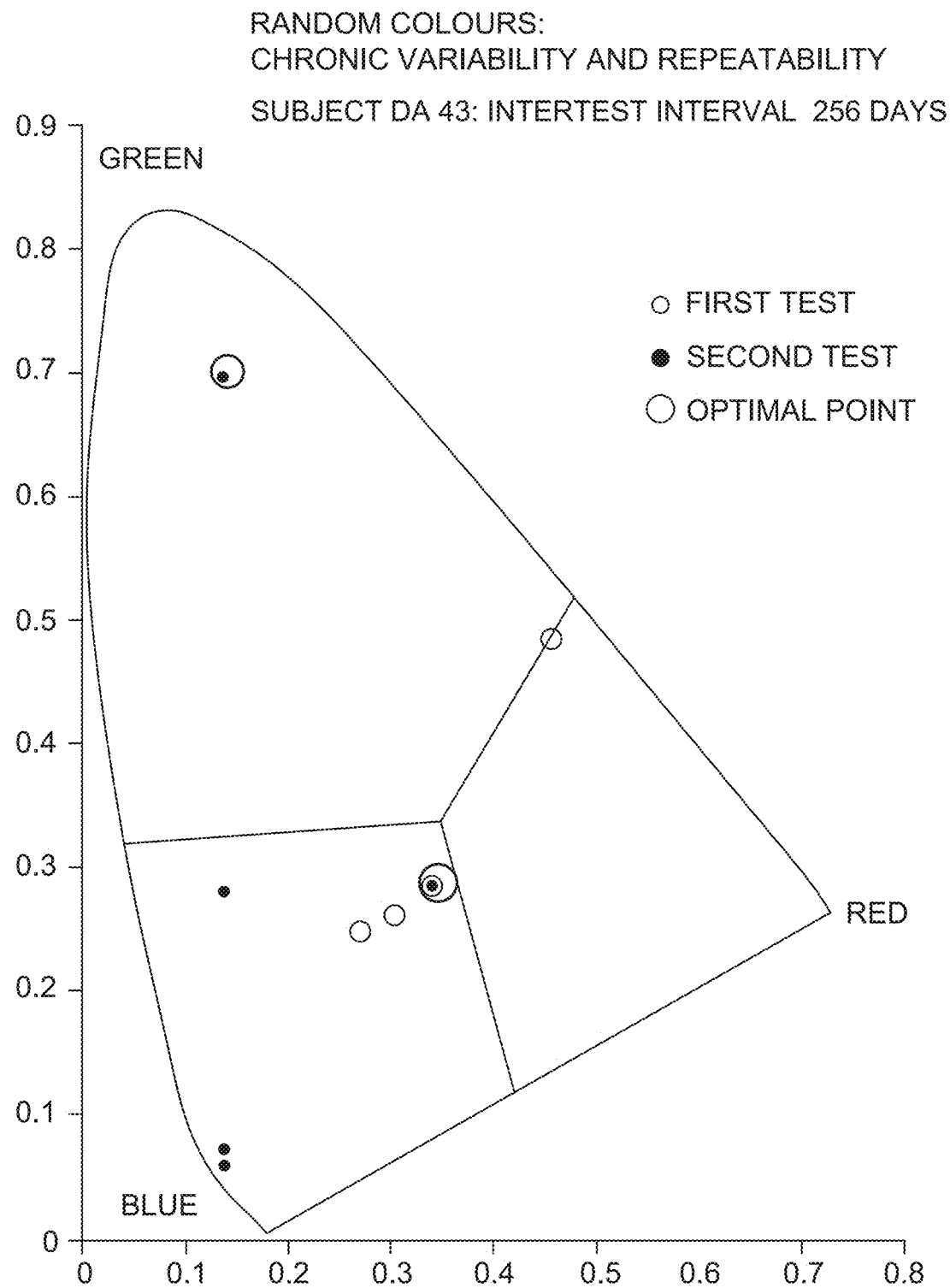
Figure 12F:
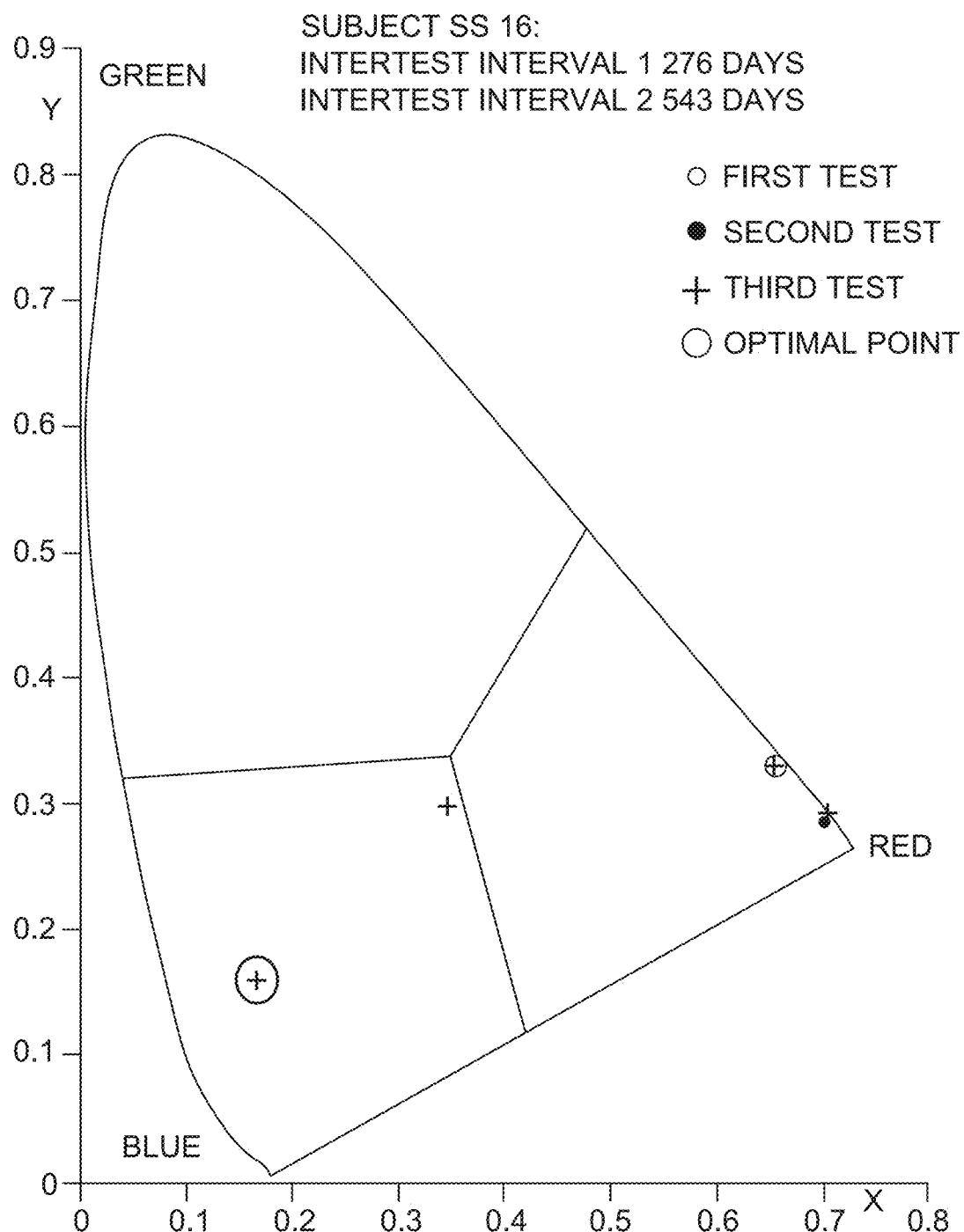
Figure 12G:
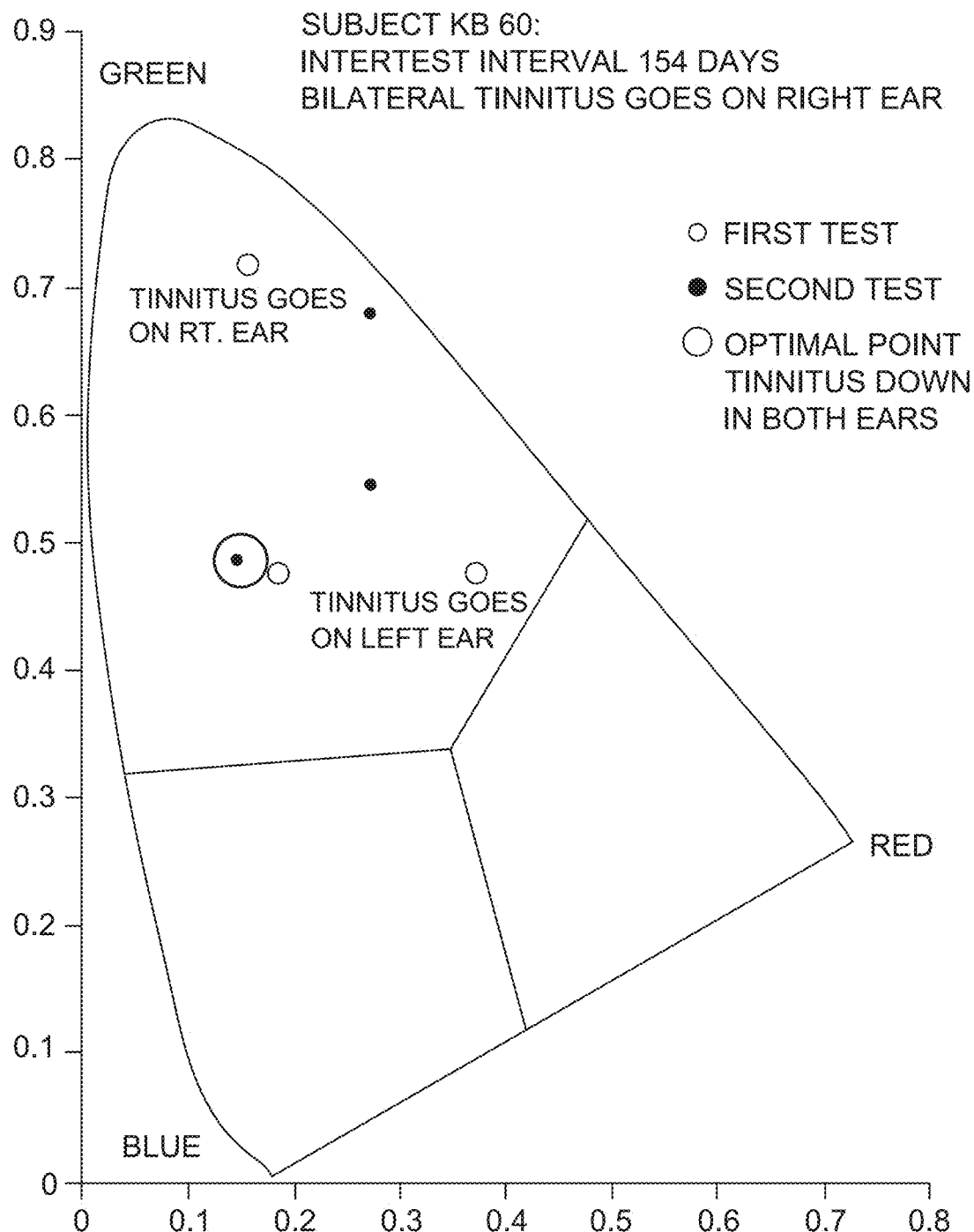

Inspection of the Figures does appear to underscore the remarkable repeatability in subjects with FIG. 10e (Subject CP56); FIG. 11b (Subject LS42); and FIG. 12f (Subject SS16) of particular note due to repeatability being observed over three sessions hundreds of days apart. This is further support for long term repeatability.

Figure 13:
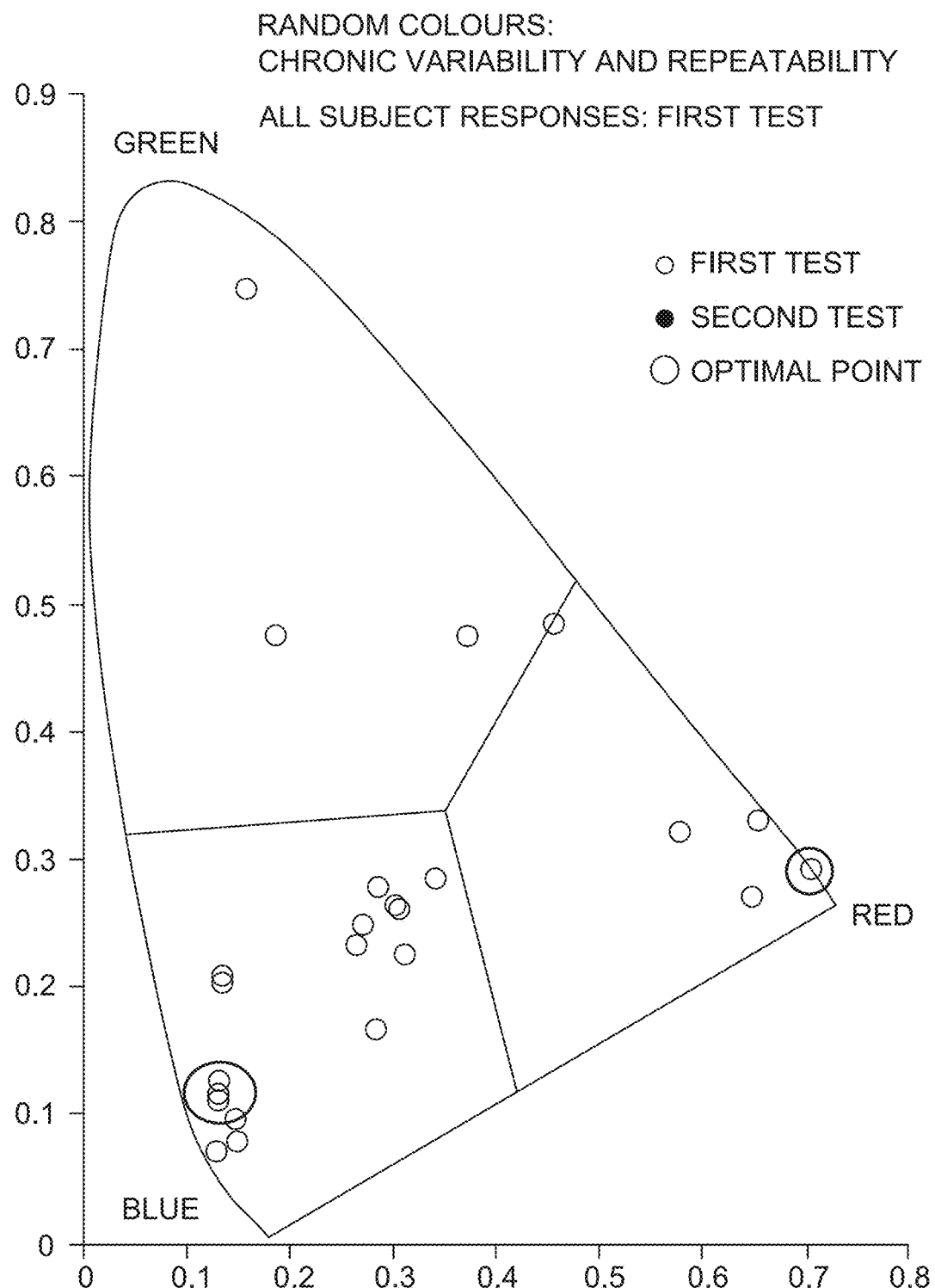
FIG. 13 is a graphical representation of a chromaticity diagram illustrating all colour points identified by all the subjects in the first chronic test.
Figure 14:
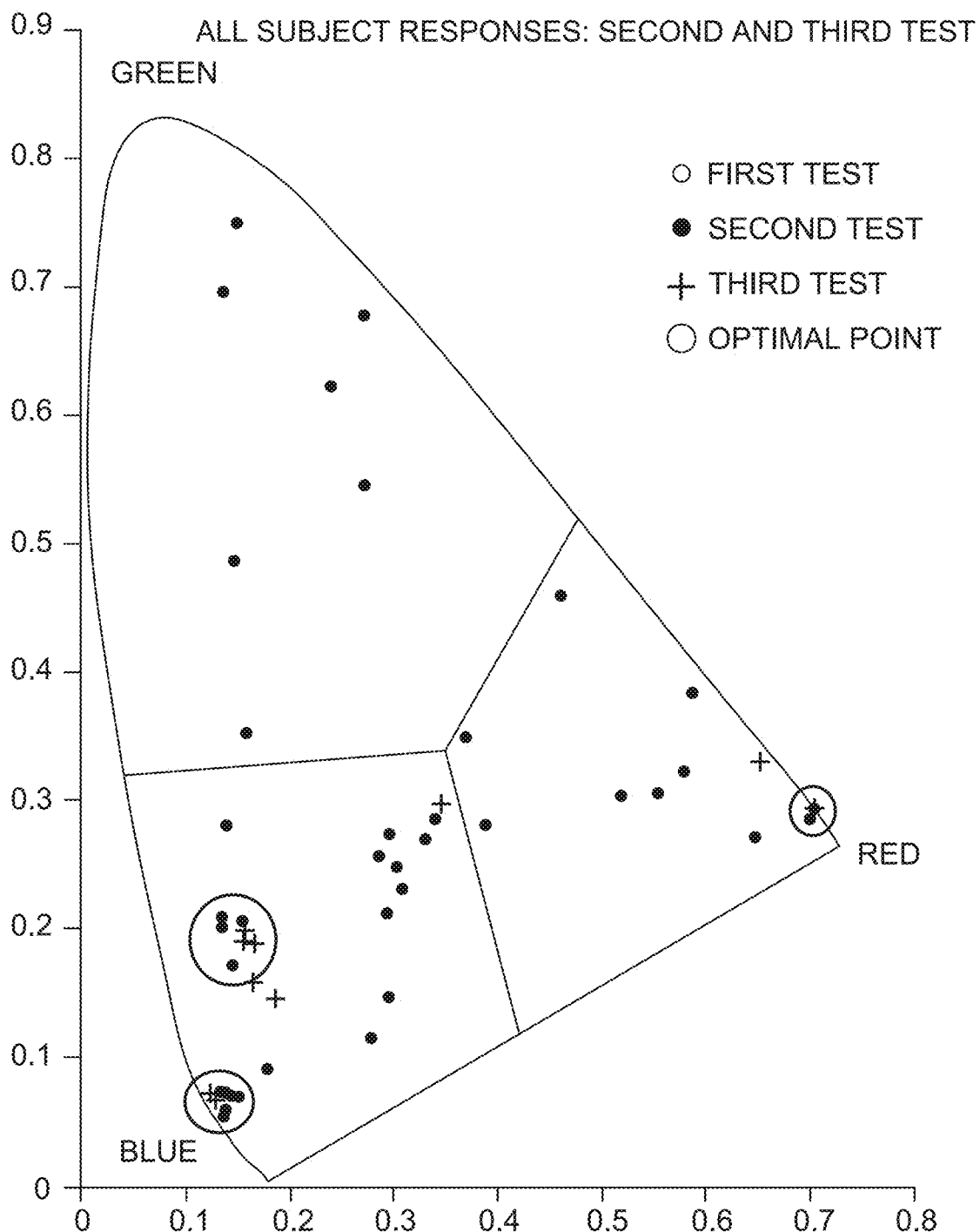
FIG. 14 is a graphical representation of a chromaticity diagram illustrating all colour points identified by all the subjects in the second chronic test.
Figure 15:
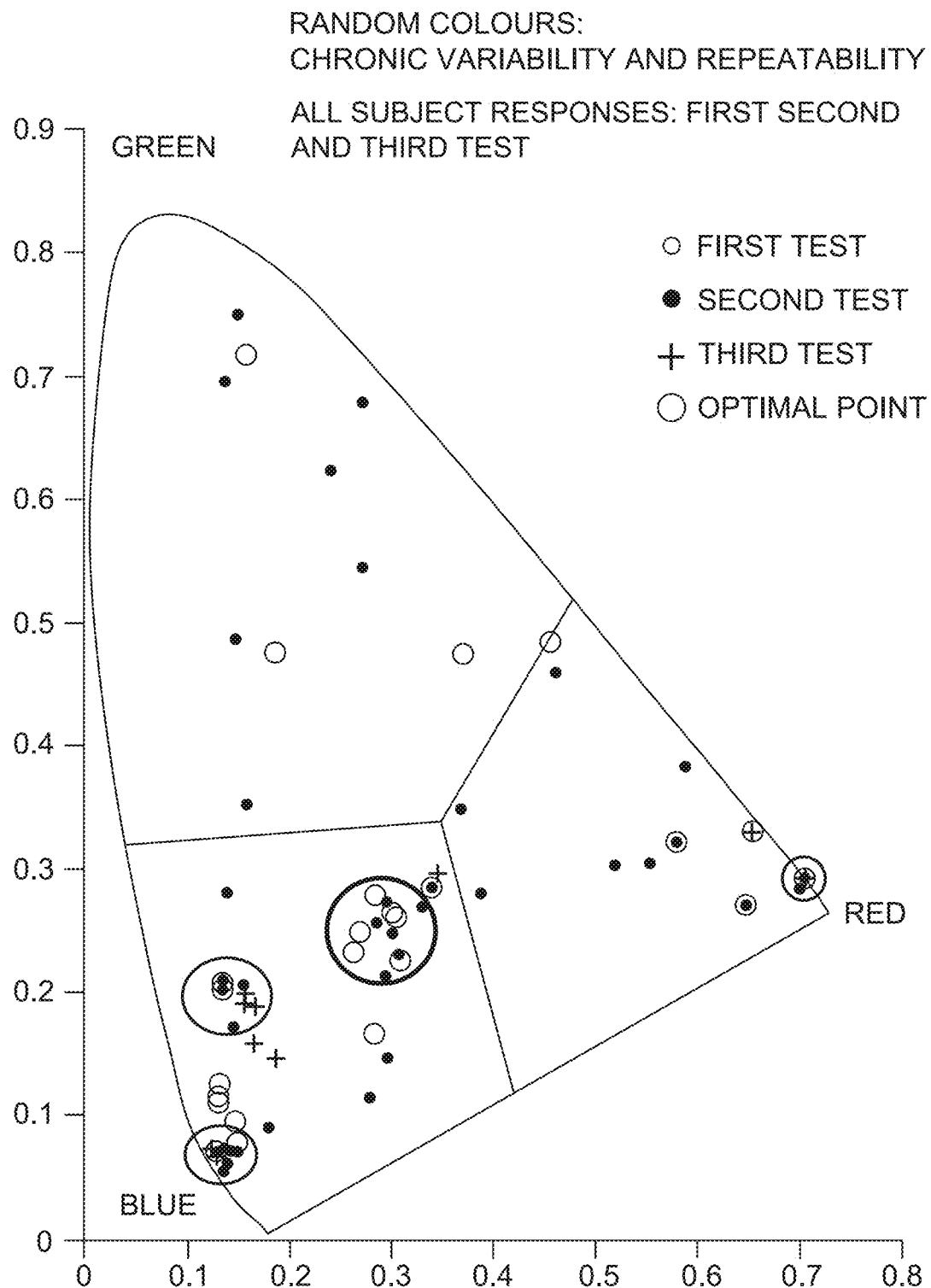
FIG. 15 is a graphical representation of a chromaticity diagram illustrating all colour points identified by all the subjects in both the first and second chronic tests.

FIGS. 13 to 15 are scatter plots illustrating all points for the first, second and, in three cases, third test in the chronic experiments. In FIGS. 13 and 14, the emergence of optimal response points for Red and Blue is partly to be expected, as seven out of fifteen of the acute subjects also took part in acute testing.

The apparent emergence of preferred optimal response points on the CIE plot is more evident on FIG. 15. With the acute results, there was one optimal response area at about X:Y co-ordinates 0.15:0.1. In this case, there are, by eye, four optimal response areas summarised in Table 4. The most prominent of these are the three 'Blue' points. The totals for these optimal points fall between 12-20% and, taken together, add up to 46/75 or 60% of total points over the three sessions.

For 'Red', the very clear preferred optimal response point centre on X:Y co-ordinates 0.706:0.294 still emerges with 4/75 or 5% of points. This compares with 8% for the acute tests, but the choice of this very particular point is still considered noteworthy. No 'Green' optimal response point was apparent in the chronic study and may reflect the lower number of total points measured.

TABLE 4

CIE Optimal Response Points from Chronic Testing

| Acute Trial | Blue X:Y | Proportion All Chronic Points | Red X:Y | Proportion All Chronic Points |
|---|---|---|---|---|
| Point 1 | 0.13:0.07 | 14/75 (19%) | 0.706:0.294 | 4/75 (5%) |
| Point 2 | 0.14:0.19 | 9/75 (12%) | | |
| Point 3 | 0.28:025 | 11/75 (15%) | | |

Acute Repeatability and Variability in Colour Distribution

In gross terms, the 15 chronic trial subjects generated a total of 24 responses in the first test and 51 responses in the second and third test combined. Gross breakdown by the 'Blue' Red' and 'Green' regions of colour space are given in Table 5.

TABLE 5

Distribution of All Acute Responses by Colour Block and Test

| Acute Trial | Blue | Red | Green | Total |
|---|---|---|---|---|
| First Test | 18 (75%) | 4 (17%) | 2 (8%) | 24 |
| Second Test | 32 (63%) | 12 (23%) | 7 (14%) | 51 |

These results show that there is some reduction in 'Blue' in the second and third chronic tests to 63%. The chronic results would still suggest the proportion of responses distributed over the CIE colours boundaries are generally consistent over the chronic test period test period over some hundreds of days.

Experiment 5: Acute Longevity of Reported Tinnitus Improvement

Of the forty one subjects reporting an improvement in their tinnitus, thirty one went on to carry out testing of acute effects over three minutes. The primary aim was to establish how changes in perception in tinnitus occurred over a short time period using a self-referenced VAS scale of 0-10, where ten was the worst imaginable and zero was absence of tinnitus.

Acute Longevity Testing

Method

Once an optimal colour (or colours) had been identified, the apparatus of the present invention was set to the X:Y co-ordinates by the experimenter. The subject was then told that their optimal colour would be presented to them over a period of three minutes. Prior to light presentation they were asked to self grade their tinnitus on a VAS scale of 0-10, where ten was the worst tinnitus they could imagine and zero represented the absence of tinnitus. Using this scale, they were then told that they would be asked by reference to this VAS value to grade their tinnitus every thirty seconds on request from the experimenter.

After a short period of about one minute of adaptation to the dark, the subject was asked to grade their tinnitus which was noted. The experimenter increased the intensity of optimal colour over 10 seconds. This intensity was held constant (with no flicker or other variation) until about 170 seconds, when it was dropped gradually to zero. At 30, 60, 90, 120, 150 and 180 seconds, the experimenter made the request to describe their tinnitus using their self-referenced VAS scale.

In a number of cases, subjects performed Longevity tests at more than one colour that they had reported to improve their tinnitus. This was done either at the same session or at a later repeat session. Only the colour producing the largest decrease in VAS was subsequently analysed.

Results: Distribution of VAS and Comparison with FEC Score.

Figure 16:
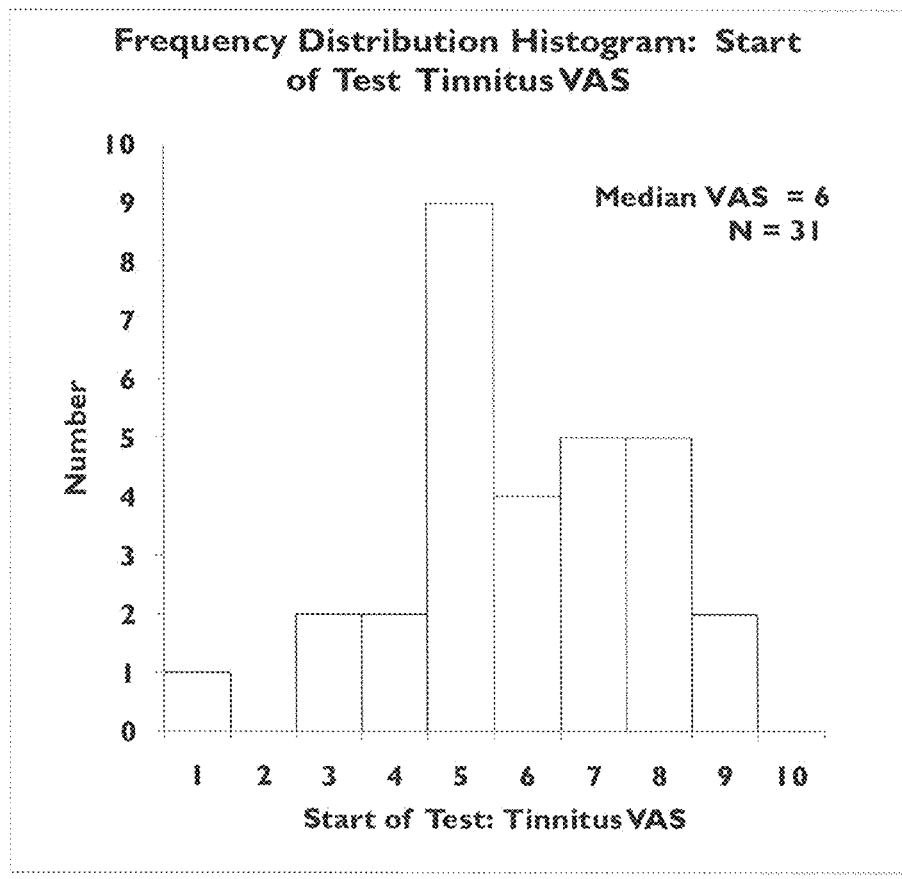
FIG. 16 is a graphical representation of the distribution of the subjects' VAS score at the start of the longevity testing.
Figure 17:
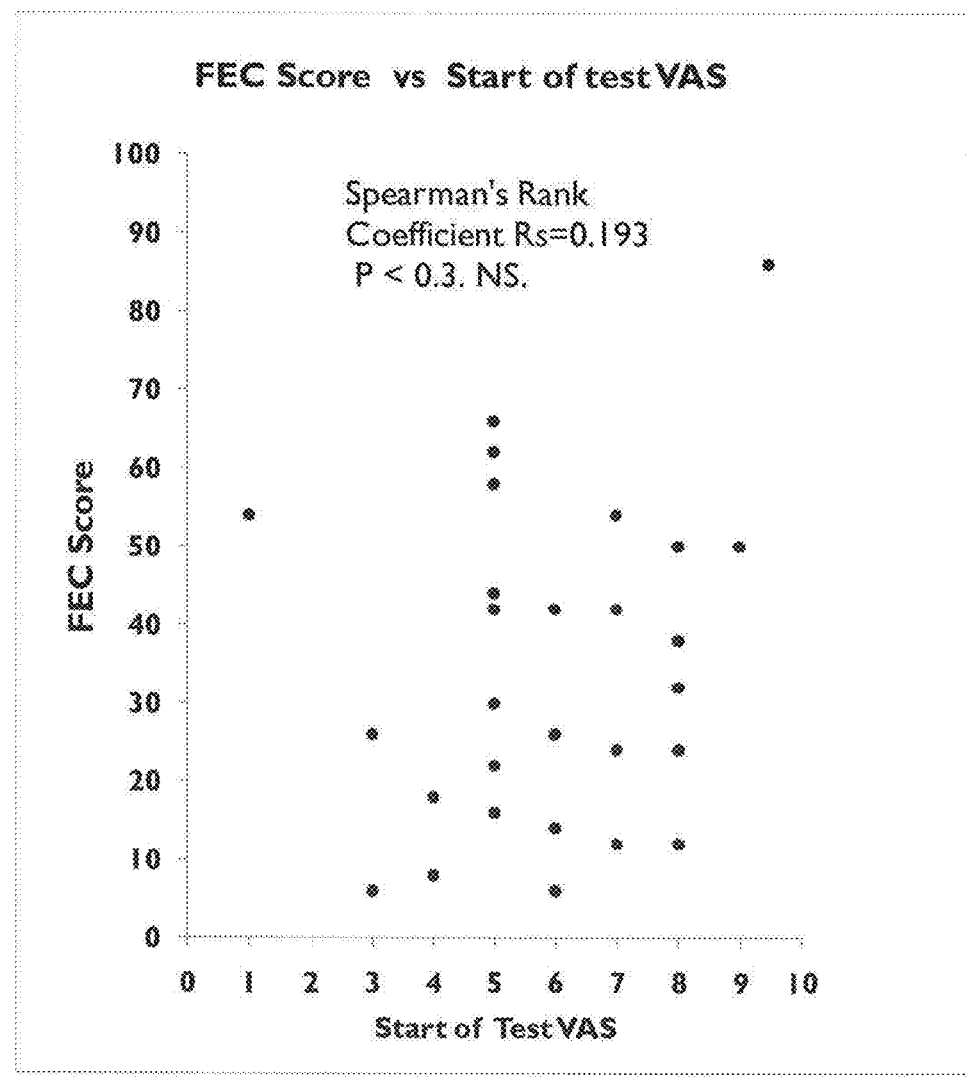
FIG. 17 illustrates a plot showing the correlation between the THI FEC score and the VAS score at the start of the longevity testing.

FIG. 16 shows the VAS distribution of 31 subjects prior to colour presentation with a median value of 6 and a range from 1 to 9. The subject reporting a value of 1 also gave unusual responses in the longevity study along with a number of others, whose VAS was not sufficient to score changes in their tinnitus. FIG. 17 also shows that in these subjects their VAS did not correlate with their FEC scores. This is evident from the widespread scatter of points so that the subject who gave a VAS of 1 has a FEC score of about 55 and others with a VAS between 6-8, have FEC scores below 30. The range of FEC scores associated with a VAS of 5 is also about 15 to 65.

Change in VAS Over Test Period

Figure 18:
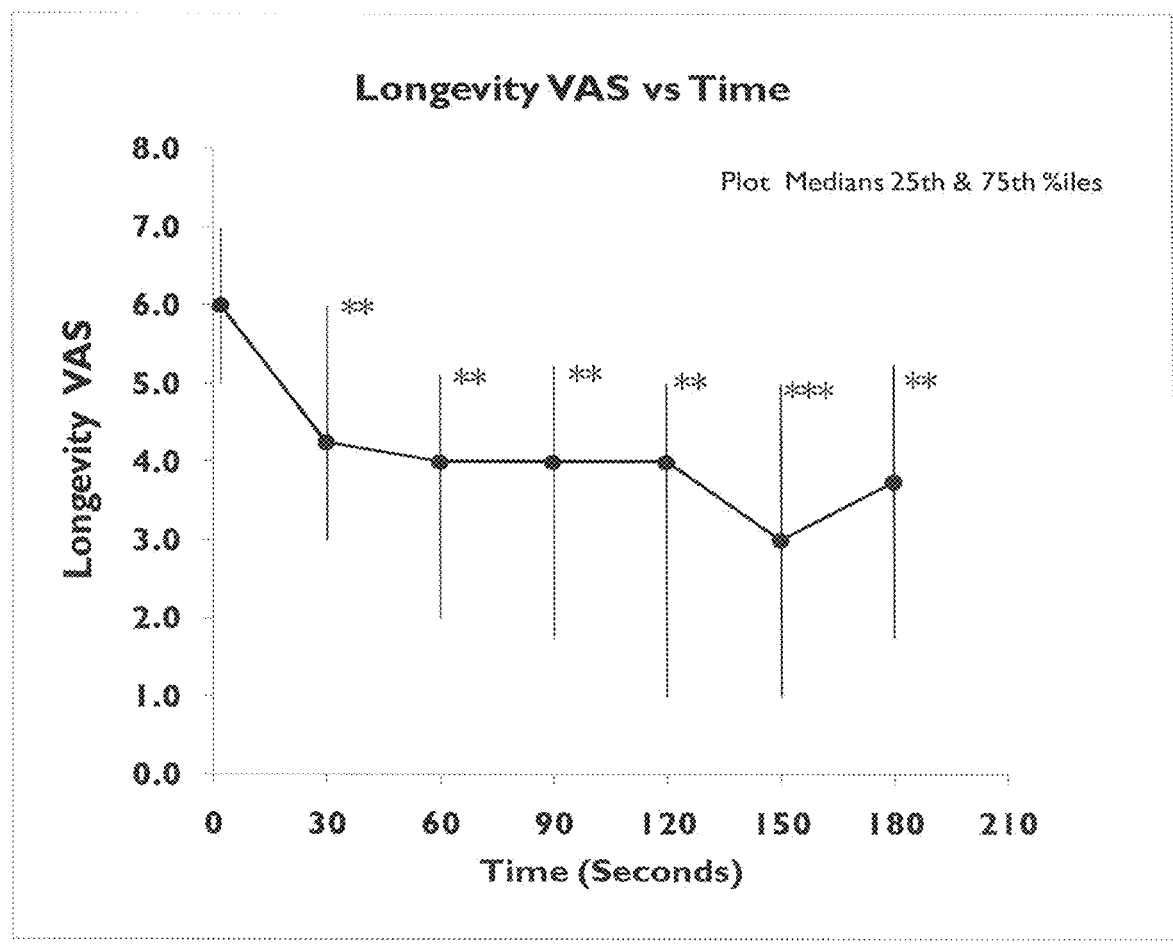
FIG. 18 illustrates a plot showing the correlation between the THI FEC score and the change in median VAS score over the longevity testing.

FIG. 18 summarises the change in median VAS over the three minute test period and shows that the median VAS ($+/-25^{th}$ & $75^{th}$ percentiles) decreased from 6 to about 4 over 30-120 seconds, with the greatest reported decrease to a median of 3 seen at 150 seconds. In percentage terms, this represents about a 35-50% decrease. The VAS began to increasing again at 180 seconds when light had just been decreased to zero intensity. Testing by Friedman's ANOVA showed overall changes to be highly significant at $p<0.00001$ with corrected pair-wise comparison significant at least $p<0.01$ throughout the test.

The Longevity data set analysed in FIG. 18 was also filtered to exclude five subjects whose VAS stayed the same or were reported as increased during testing. Inclusion of these results in the analysis still resulted in a highly significantly decrease in median VAS across all time points, but was the median shifts were reduced.

Maximal Changes in VAS over Test Period

Figure 19:
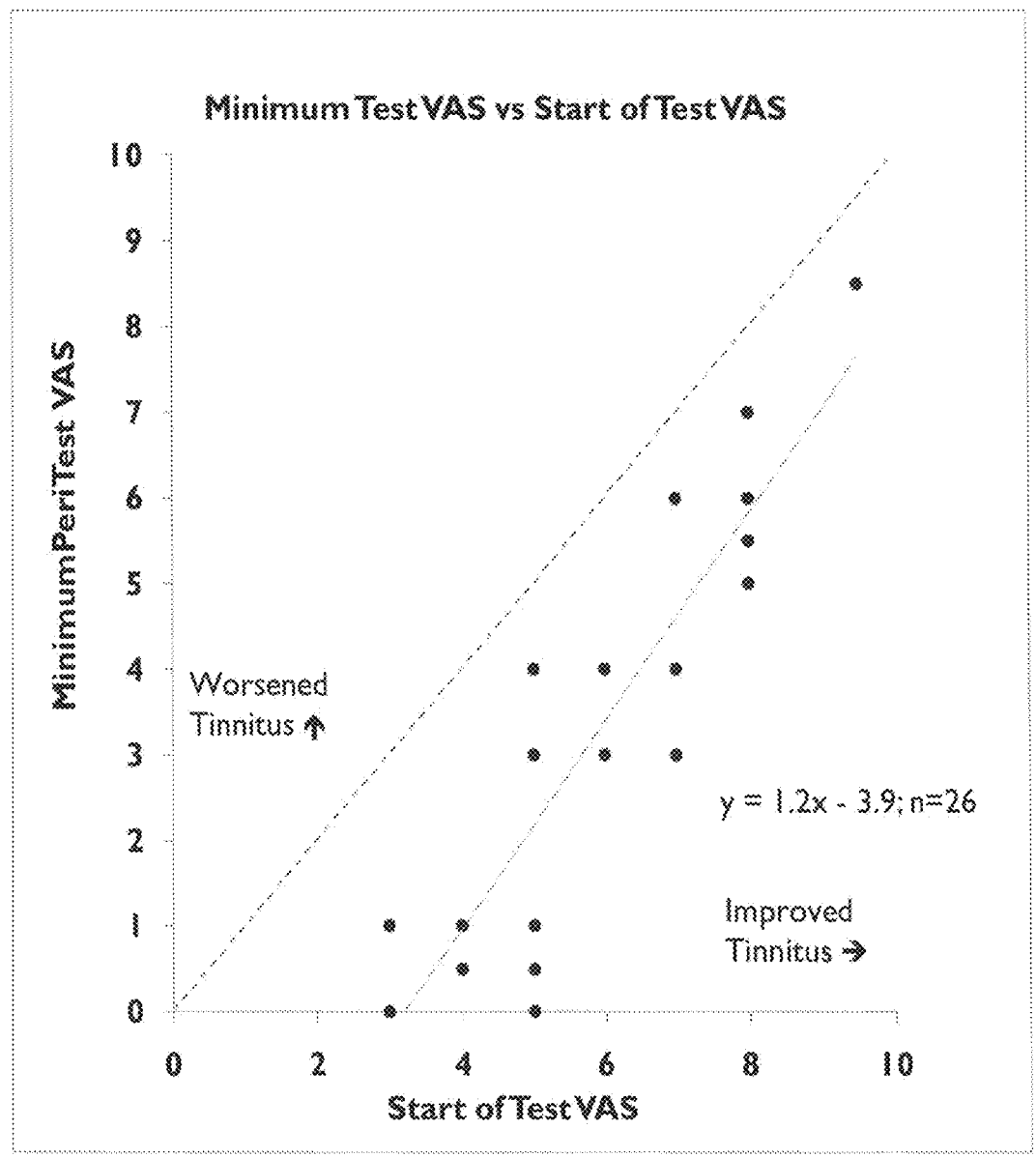
FIG. 19 illustrates a plot showing the correlation between the minimum VAS score during the longevity testing and the VAS score at the start of the test.

FIG. 19 plots individual filtered data (n=26) as the minimum VAS attained at any time point over the acute test period vs the initial start VAS. The dotted diagonal line represents the line of which no change occurs, i.e. with a nominal gradient=1. Any values above this line would represent a worsening of tinnitus, whilst those increasingly further away to the right of the line represent an increasing improvement of the tinnitus. The data plotted in this manner also reveal any relationship in categorical magnitude between control and peritest VAS. Whilst the data have to be interpreted cautiously, it appears that subjects with a pre-test VAS between 3-5 have the relatively greatest proportionate change in tinnitus intensity and the degree of VAS reduction drops with higher pre-test scores with this limited data set.

Figure 20:
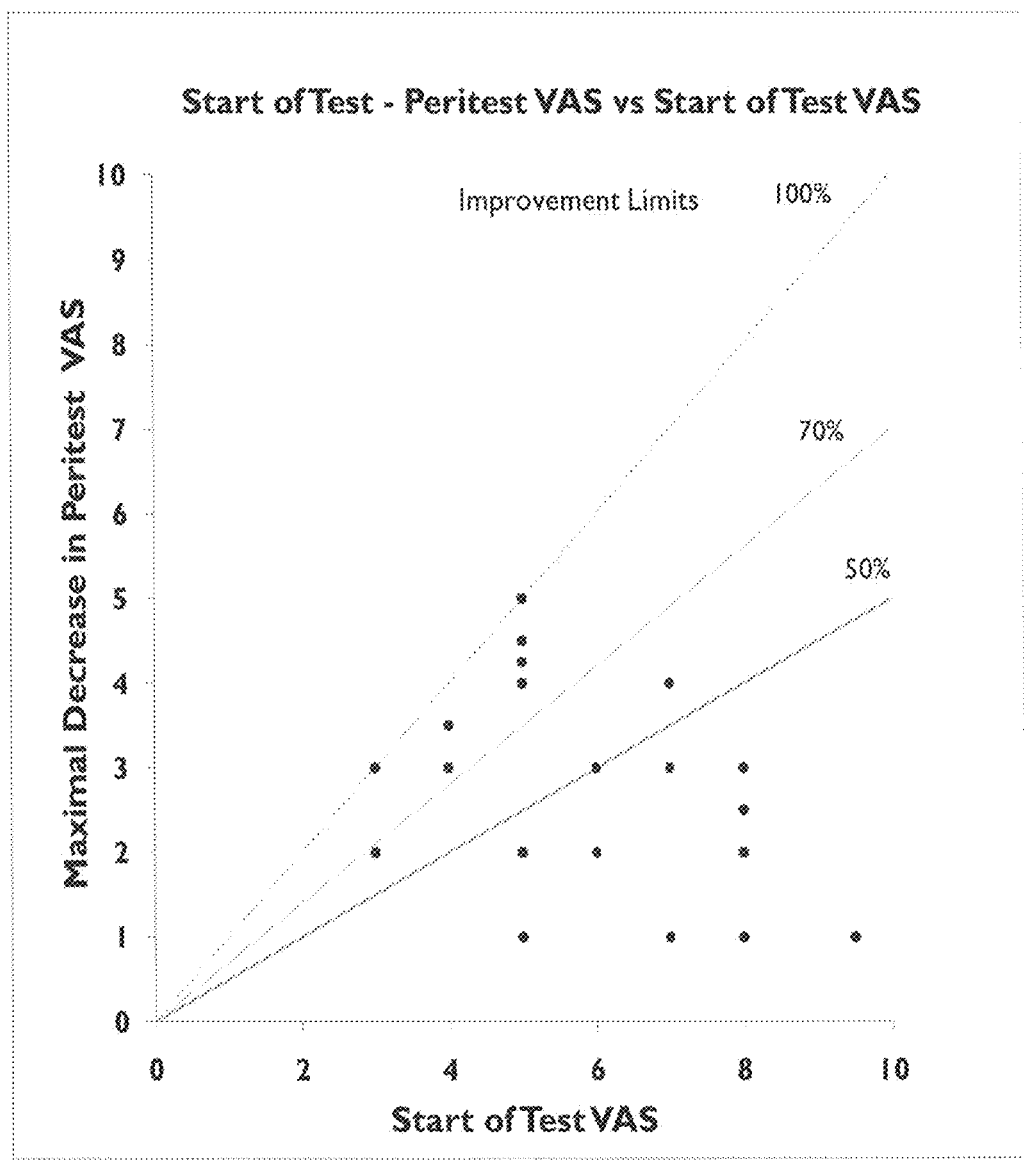
FIG. 20 illustrates a plot showing the difference in the minimum VAS score in terms of the VAS score at the start of the test and the VAS score during longevity testing.

Expressed as a maximal change, i.e. Pre test—Peritest VAS in FIG. 20, provides a further way of considering relative change. In general terms, this shows that those patients with a pre-test VAS of between 3-5 reported up to a 70-100% decrease in category. This was for 8/31 or about 25% subjects. Of the rest 13/31 or about 40% reported a percentage decrease in category of between 25-70%, 5/31 or about 15% reported a percentage decrease in VAS category between 10-25%.

These results appear to be in line with the acute longevity changes in medians from 6 to 4 or a median decrease of about 35%.

The experimental data clearly shows that tinnitus sufferers have achieved alleviation in the perception of their tinnitus when subjected to coloured light at one or more points in colour space. In particular, the data shows that coloured light may be used to treat all categories of tinnitus sufferers, providing much improved success rates compared to existing treatments for tinnitus. This therefore demonstrates that coloured light can be used to alleviate the symptoms of tinnitus in accordance with the present invention.

The invention claimed is:

1. A method of assessing an effect of viewing varying colors of light on a subject's perception of tinnitus, comprising the steps of:
   presenting a display in at least part of a subject's field of view;
   illuminating the display with a visual stimulus, the visual stimulus consisting of colored light in a visible spectrum using one or more variable sources;
   varying measurable values of the colored light illuminating the display;
   recording the measurable values of the colored light illuminating the display at which the subject indicates a change in their perception of tinnitus; and providing a tuned light source formulated to output colored light having the measurable values for observation by the subject.

2. The method according to claim 1 wherein said measurable values are tristimulus values of the colored light entering a subject's eye.

3. The method according to claim 1 wherein said measurable values are mixtures of wavelengths making up the colored light.

4. The method according to claim 1 wherein said one or more variable sources comprise one or more narrowband colored light sources.

5. The method according to claim 1 wherein said one or more variable sources is in a form of a color controllable light source having at least two narrowband colored light sources which each emit different spectral components within the visible light spectrum.

6. The method according to claim 1 wherein the steps of claim 1 are repeated at least once.

7. A method comprising:
   obtaining recorded measurable values of visual stimulus, the visual stimulus consisting of colored light illuminating a display presented in at least part of a subject's field of view, the recorded measureable values corresponding to the subject indicating a change in a perception of tinnitus; and
   providing a customized, calibrated, tuned article formulated to modify illumination of at least part of the field of view of the subject such that colored light having the recorded measurable values determined by the method is observable by the subject.

8. The method of claim 7, wherein the customized, calibrated, tunable article is a calibrated, tunable light source.

9. The method of claim 7, wherein the customized, calibrated, tunable article is a customized filter.

10. A method of assessing an effect of viewing varying colors of light on a subject's perception of tinnitus, comprising the steps of:
    presenting a display in at least part of a subject's field of view;
    illuminating the display with a visual stimulus, the visual stimulus consisting of colored light in a visible spectrum using one or more variable sources;
    varying measurable values of the colored light illuminating the display;
    recording the measurable values of the colored light illuminating the display at which the subject indicates a change in their perception of tinnitus; and
    providing a customized filter formulated to modify illumination of at least part of the field of view of the subject such that colored light having the measurable values is observed by the subject.

11. The method according to claim 10 wherein said measurable values are tristimulus values of the colored light entering a subject's eye.

12. The method according to claim 10 wherein said measurable values are mixtures of wavelengths making up the colored light.

13. The method according to claim 10 wherein said one or more variable sources comprise one or more narrowband colored light sources.

14. The method according to claim 10 wherein said one or more variable sources is in a form of a color controllable light source having at least two narrowband colored light sources which each emit different spectral components within the visible light spectrum.

15. The method according to claim 10 wherein the steps of claim 10 are repeated at least once.

* * * * *